(12) United States Patent
Bhide et al.

(10) Patent No.: US 6,951,859 B2
(45) Date of Patent: Oct. 4, 2005

(54) PYRROLOTRIAZINE KINASE INHIBITORS

(75) Inventors: Rajeev S. Bhide, Princeton Junction, NJ (US); Robert M. Borzilleri, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/633,997

(22) Filed: Aug. 4, 2003

(65) Prior Publication Data

US 2004/0063708 A1 Apr. 1, 2004

Related U.S. Application Data

(60) Provisional application No. 60/400,572, filed on Aug. 2, 2002.

(51) Int. Cl.$^7$ .................. C07D 487/04; A61K 31/53; A61P 35/00
(52) U.S. Cl. ........................ 514/243; 544/183
(58) Field of Search ................... 544/183; 514/243

(56) References Cited

U.S. PATENT DOCUMENTS

2003/0069244 A1  4/2003  Leftheris et al.

FOREIGN PATENT DOCUMENTS

WO    WO 02/40486    5/2002

OTHER PUBLICATIONS

Cecil Textbook of Medicine, edited by Bennet, J.C., and Plum F., 20th edition, vol. 1, 1004–1010, 1996.*
Wolft Manfred E. "Burger's Medicinal Chemistry, 5ed, Part 1", John Wiley & Sons, 1995, pp. 975–977.*
Banker, G.S. et al, "Modern Pharmaceutics, 3ed.", Marcel Dekker, New York. 1996, pp. 451 and 596.*
West, Anthony R., Solid State Chemistry and its Applications, Wiley, New York, 1988, pp. 358 & 365.*
Fan et al., Trend Pharmacol. Sci., vol. 16, pp. 57–66 (1995).
Folkman, Nature Medicine, vol. 1, pp. 27–31 (1995).
Cullinan–Bove et al., Endocrinology, vol. 133, pp. 829–837 (1993).
Senger et al., Cancer and Metastasis Reviews, vol. 12, pp. 303–324 (1993).
DeVries et al., Science, vol. 255, pp. 989–991 (1992).
Terman et al., Biochem. Biophys. Res. Comm., vol. 187, pp. 1579–1586 (1992).
Jakeman et al., Endocrionology, vol. 133, pp. 848–859 (1993).
Kolch et al., Breast Cancer Research and Treatment, vol. 36, pp. 139–155 (1995).
Connolly et al., J. Biol. Chem., vol. 264, pp. 20017–20024 (1989).
U.S. Appl. No. 10/289,010, filed Nov. 6, 2002, Godfrey et al., pending.
U.S. Appl. No. 09/573,829, filed May 18, 2000, Hant et al., pending.
U.S. Appl. No. 10/294,281, filed Nov. 14, 2002, Mastalerz et al., pending.
U.S. Appl. No. 10/623,171, filed Jul. 18, 2003, Bhide et al., pending.
U.S. Appl. No. 10/420,399, filed Apr. 22, 2003, Dyckman et al., pending.
U.S. Appl. No. 10/420,445, filed Apr. 22, 2003, Dyckman et al., pending.
U.S. Appl. No. 10/440,864, filed May 19, 2003, Das et al., pending.

* cited by examiner

Primary Examiner—Venkataraman Balasubramanian
(74) Attorney, Agent, or Firm—Elliott Korsen

(57) ABSTRACT

The present invention provides compounds of formula I,

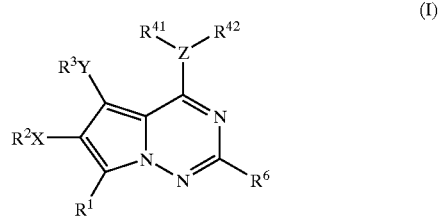

and pharmaceutically acceptable salts thereof.

The formula I compounds inhibit the tyrosine kinase activity of growth factor receptors such as VEGFR-2 and FGFR-1, thereby making them useful as anti-cancer agents. The formula I compounds are also useful for the treatment of other diseases associated with signal transduction pathways operating through growth factor receptors.

2 Claims, No Drawings

PYRROLOTRIAZINE KINASE INHIBITORS

This application claims priority to U.S. Provisional Application Ser. No. 60/400,572 filed Aug. 2, 2002, the entire content of which is incorporated herein by reference.

FIELD OF THE INVENTION

This invention relates to compounds that inhibit the tyrosine kinase activity of growth factor receptors such as VEGFR-2, and FGFR-1, thereby making them useful as anti-cancer agents. The compounds are also useful in the treatment of diseases, other than cancer, which are associated with signal transduction pathways operating through growth factor and anti-angiogenesis receptors such as VEGFR-2.

BACKGROUND OF THE INVENTION

Normal angiogenesis plays an important role in a variety of processes including embryonic development, wound healing, obesity and several components of female reproductive function. Undesirable or pathological angiogenesis had been associated with disease states including diabetic retinopathy, psoriasis, rheumatoid arthritis, atheroma, Kaposi's sarcoma and haemangioma, asthma, cancer and metastatic disease (Fan et al, 1995, Trend Pharmacol. Sci. 16: 57–66; Folkman, 1995, Nature Medicine 1: 27–31). Alteration of vascular permeability is thought to play a role in both normal and pathophysiological processes (Cullinan-Bove et al, 1993, Endocrinology 133: 829–837; Senger et al, 1993 Cancer and Metastasis Reviews, 12: 303–324).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity that leads to phosphorylation of tyrosine residues on both the receptor and other intracellular proteins, leading to a variety of cellular responses. To date, at least nineteen distinct RTK subfamilies, defined by amino acid sequence homology, have been identified. One of these subfamilies is presently comprised of the fms-like tyrosine kinase receptor, Flt or Flt1 (VEGFR-1), the kinase insert domain-containing receptor, KDR (also referred to as Flk-1 or VEGFR-2), and another fms-like tyrosine kinase receptor, Flt4 (VEGFR-3). Two of these related RTKs, Flt and KDR, have been shown to bind vascular endothelial growth factor (VEGF) with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells had been associated with changes in the tyrosine phosphorylation status of cellular proteins and calcium fluxes. VEGF, along with acidic and basic fibroblast growth factor (aFGF & bFGF) have been identified as having in vitro endothelial cell growth promoting activity. It is noted that aFGF and bFGF bind to and activate the receptor tyrosine kinase termed FGFR-1. By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36: 139–155) and vascular permeability (Connolly et al, 1989, J. Biol. Chem. 264: 20017–20024).

In adults, endothelial cells have a low proliferation index except in cases of tissue remodeling, such as wound healing and the female reproductive cycle, and adipogenesis. However in pathological states such as cancer, inherited vascular diseases, endometriosis, psoriasis, arthritis, retinopathies and atherosclerosis, endothelial cells are actively proliferating and organizing into vessels. Upon exposure to angiogenic stimuli with growth factors such as VEGF and bFGF, endothelial cells re-enter the cell cycle, proliferate, migrate and organize into a three-dimensional network. It is now widely accepted that the ability of tumors to expand and metastasize is dependent upon the formation of this vascular network.

Binding of VEGF or bFGF to their corresponding receptor results in dimerization, autophosphorylation on tyrosine residues and enzymatic activation. These phosphotyrosine residues serve as "docking" sites for specific downstream signaling molecules and enzymatic activation results in EC activation. Disruption of these pathways should inhibit endothelial cell activation. Disruption of the FGFR-1 pathway should also affect tumor cell proliferation since this kinase is activated in many tumor types in addition to proliferating endothelial cells. Finally, recent evidence also suggests that disruption of VEGF signaling inhibits endothelial cell migration, a critical process in vascular network formation.

The over-expression and activation of VEGFR-2 and FGFR-1 in tumor-associated vasculature has suggested a role for these molecules in tumor angiogenesis. Angiogenesis and subsequent tumor growth is inhibited by antibodies directed against VEGF ligand and VEGF receptors, and by truncated (lacking a transmembrane sequence and cytoplasmic kinase domain) soluble VEGFR-2 receptors. Dominant mutations introduced into either VEGFR-2 or FGFR-1 which result in a loss of enzymatic activity inhibits tumor growth in vivo. Antisense targeting of these receptors or their cognate ligands also inhibits angiogenesis and tumor growth. Recent evidence has elucidated, in part, the temporal requirements of these receptors in tumor growth. It appears that VEGF signaling is critical in early tumor growth and bFGF is more important at a later time associated with tumor expansion.

DETAILED DESCRIPTION OF THE INVENTION

In accordance with the present invention, compounds of formula I,

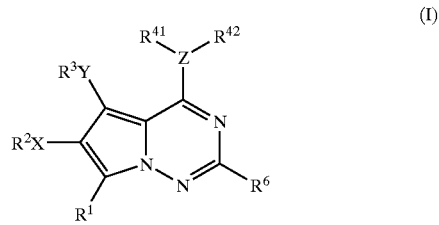

their enantiomers, diastereomers, and pharmaceutically acceptable salts, prodrugs and solvates thereof, inhibit the tyrosine kinase activity of growth factor receptors such as VEGFR-2.

In formula I and throughout the specification, the above symbols are defined as follows:

Z is selected from O, S, N, OH, or Cl, with the provisos that when Z is O or S, $R^{41}$ is absent and when Z is OH or Cl, both $R^{41}$ and $R^{42}$ are absent and when Z is N, then $R^{41}$ is H;

X and Y are independently selected from O, OCO, S, SO, $SO_2$, CO, $CO_2$, $NR^{10}$, $NR^{11}CO$, $NR^{12}CONR^{13}$, $NR^{14}CO_2$, $NR^{15}SO_2$, $NR^{16}SO_2NR^{17}$, $SO_2NR^{18}$, $CONR^{19}$, halogen, nitro, cyano, or X or Y are absent;

$R^1$ is hydrogen, $CH_3$, OH, $OCH_3$, SH, $SCH_3$, $OCOR^{21}$, $SOR^{22}$, $SO_2R^{23}$, $SO_2NR^{24}R^{25}$, $CO_2R^{26}$, $CONR^{27}R^{28}$, $NH_2$, $NR^{29}SO_2NR^{30}R^{31}$, $NR^{32}SO_2R^{33}$, $NR^{34}COR^{35}$, $NR^{36}CO_2R^{37}$, $NR^{38}CONR^{39}R^{40}$, halogen, nitro, or cyano;

$R^2$ and $R^3$ are independently hydrogen, alkyl, substituted alkyl, alkenyl, substituted alkenyl, alkynyl, substituted alkynyl, aryl, substituted aryl, heterocyclo, substituted heterocyclo, aralkyl, substituted aralkyl, heterocycloalkyl or substituted heterocycloalkyl, or when X is halo, nitro or cyano $R^2$ is absent or when Y is halo, nitro or cyano $R^3$ is absent;

$R^6$ is H, alkyl, substituted alkyl, aryl, substituted aryl, heterocyclo, substituted heterocyclo, $NR^7R^8$, $OR^9$ or halogen;

$R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{24}$, $R^{25}$, $R^{26}$, $R^{27}$, $R^{28}$, $R^{29}$, $R^{30}$, $R^{31}$, $R^{32}$, $R^{34}$, $R^{35}$, $R^{36}$, $R^{38}$, $R^{39}$ and $R^{40}$ are independently selected from the group consisting of hydrogen, alkyl, substituted alkyl, aryl, substituted aryl, heterocyclo, or substituted heterocyclo;

$R^{22}$, $R^{23}$, $R^{33}$ and $R^{37}$ are independently selected from the group consisting of alkyl, substituted alkyl, aryl, substituted aryl, heterocyclo, or substituted heterocyclo;

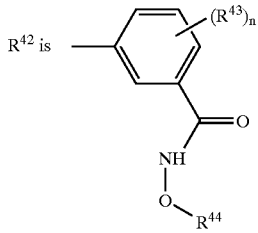

wherein
each $R^{43}$ is independently selected from fluorine or methyl;
n is 0, 1 or 2; and
$R^{44}$ is methyl, ethyl or cyclopropylmethyl;
with the further provisos that:
a. $R^2$ may not be hydrogen if X is SO, $SO_2$, $NR^{13}CO_2$, or $NR^{14}SO_2$, and
b. $R^3$ may not be hydrogen if Y is SO, $SO_2$, $NR^{13}CO_2$, or $NR^{14}SO_2$.

Preferred compounds of the invention include:
[4-[[2,4-Difluoro-5-[(methoxyamino)carbonyl]phenyl]amino]-5-(1-methylethyl)pyrrolo[2,1-f][1,2,4]triazin-6-yl]carbamic acid 3-(methylsulfonyl)propyl ester,
[4-[[2,4-Difluoro-5-[(methoxyamino)carbonyl]phenyl]amino]-5-(1-methylethyl)pyrrolo[2,1-f][1,2,4]triazin-6-yl]carbamic acid 3-(1-piperidinyl)propyl ester,
5-[[6-[5-(Difluoromethyl)-1,3,4-oxadiazol-2-yl]-5-(1-methylethyl)pyrrolo [2, 1-f][1,2,4]triazin-4-yl]amino]-2,4-difluoro-N-methoxybenzamide,
2,4-Difluoro-N-methoxy-5-[[5-(1-methylethyl)-6-(2-methyl-1H-1,2,4-triazol-3-yl)pyrrolo[2,1-f][1,2,4]triazin-4-yl]amino]benzamide,
2,4-Difluoro-N-methoxy-5-[[5-(1-methylethyl)-6-[5-[(methylsulfonyl)methyl]-1,3,4-oxadiazol-2-yl]pyrrolo[2,1-f][1,2,4]triazin-4-yl]amino]benzamide,
5-[[6-[5-[Difluoro(methylsulfonyl)methyl]-1,3,4-oxadiazol-2-yl]-5-(1-methylethyl)pyrrolo[2,1-f][1,2,4]triazin-4-yl]amino]-2,4-difluoro-N-methoxybenzamide,
5-[[6-[5-(Dimethylamino)-1,3,4-oxadiazol-2-yl]-5-(1-methylethyl)pyrrolo[2,1-f][1,2,4]triazin-4-yl]amino]-2,4-difluoro-N-methoxybenzamide,
4-Fluoro-N-methoxy-3-[[5-(1-methylethyl)-6-(5-methyl-2-oxazolyl)pyrrolo[2,1-f][1,2,4]triazin-4-yl]amino]benzamide,
2,4-Difluoro-N-methoxy-5-[[5-(1-methylethyl)-6-(5-methyl-2-oxazolyl)pyrrolo[2,1-f][1,2,4]triazin-4-yl]amino]benzamide, and
2,4-Difluoro-N-methoxy-5-[[5-(1-methylethyl)-6-(5-methyl-1,2,4-oxadiazol-3-yl)pyrrolo[2,1-f][1,2,4]triazin-4-yl]amino]benzamide.

The invention also provides a pharmaceutical composition comprising a compound of formula I and a pharmaceutically acceptable carrier.

The invention also provides a pharmaceutical composition comprising a compound of formula I in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin; razoxane; tamoxifen; toremifene; raloxifene; droloxifene; iodoxifene; megestrol acetate; anastrozole; letrozole; borazole; exemestane; flutamide; nilutamide; bicalutamide; cyproterone acetate; gosereline acetate; leuprolide; finasteride; metalloproteinase inhibitors; inhibitors of urokinase plasminogen activator receptor function; growth factor antibodies; growth factor receptor antibodies such as Avastin® (bevacizumab) and Erbitux® (cetuximab); tyrosine kinase inhibitors; serine/threonine kinase inhibitors; methotrexate; 5-fluorouracil; purine; adenosine analogues; cytosine arabinoside; doxorubicin; daunomycin; epirubicin; idarubicin; mitomycin-C; dactinomycin; mithramycin; cisplatin; carboplatin; nitrogen mustard; melphalan; chlorambucil; busulphan; cyclophosphamide; ifosfamide nitrosoureas; thiotepa; vincristine; Taxol® (paclitaxel); Taxotere® (docetaxel); epothilone analogs; discodermolide analogs; eleutherobin analogs; etoposide; teniposide; amsacrine; topotecan; flavopyridols; biological response modifiers and proteasome inhibitors such as Velcade® (bortezomib).

The invention also provides a method of inhibiting protein kinase activity of growth factor receptors which comprises administering to a mammalian species in need thereof, a therapeutically effective protein kinase inhibiting amount of a compound of formula I.

Additionally, there is disclosed a method of inhibiting tyrosine kinase activity of at least one growth factor receptor such as which comprises administering to a mammalian species in need thereof, a therapeutically effective amount of a compound of formula I. In a preferred embodiment said growth factor receptor is selected from the group consisting of VEGFR-2 and FGFR-1.

Finally, there is disclosed a method for treating a proliferative disease, comprising administering to a mammalian species in need thereof, a therapeutically effective amount of a compound of formula I. In a preferred embodiment the proliferative disease is cancer.

Definitions

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, benzimidazole, dihydrobenzofuryl, indolyl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclos, such as, epoxides and aziridines.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of formula I may also have prodrug forms. Any compound that will be converted in vivo to provide the bioactive agent (i.e., the compound for formula I) is a prodrug within the scope and spirit of the invention.

Various forms of prodrugs are well known in the art. For examples of such prodrug delivery derivatives, see:

a) *Design of Prodrugs*, H. Bundgaard (editor), Elsevier (1985);

b) *Methods in Enzymology*, K. Widder et al. (editors), Academic Press, Vol. 42, 309–396 (1985);

c) *A Textbook of Drug Design and Development*, Krosgaard-Larsen and H. Bundgaard (editors), Chapter 5, "Design and Application of Prodrugs," 113–191 (1991);

d) H. Bundgaard, *Advanced Drug Delivery Reviews*, 8, 1–38 (1992);

e) H. Bundgaard, *J. of Pharm. Sciences*, 77, 285 (1988); and f) N. Kakeya et al., *Chem. Pharm. Bull.*, 32 692 (1984).

It should further be understood that solvates (e.g., hydrates) of the compounds of formula I are also with the scope of the present invention. Methods of solvation are generally known in the art.

Use and Utility

The present invention is based on the discovery that certain pyrrolotriazines are inhibitors of protein kinases. More specifically, they inhibit the effects of VEGF, a property of value in the treatment of disease states associated with angiogenesis and/or increased vascular permeability such as cancer. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with VEGF, especially those tumors which are significantly dependent on VEGF for their growth and spread, including for example, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung. In another embodiment, the compounds of the present invention are also useful in the treatment of noncancerous disorders such as diabetes, diabetic retinopathy, psoriasis, rheumatoid arthritis, obesity, Kaposi's sarcoma, haemangioma, acute and chronic nephropathies (including proliferative glomerulonephritis and diabetes-induced renal disease), atheroma, arterial restenosis, autoimmune diseases, acute inflammation and ocular diseases with retinal vessel proliferation, diabetic retinopathy, retinopathy of prematurity and macular degeneration. The invention also relates to prevention of blastocyte implantation in a mammal, treatment of atherosclerosis, eczema, scleroderma, hemangioma. Compounds of the present invention posses good activity against VEGF receptor tyrosine kinase while possessing some activity against other tyrosine kinases.

Thus according to a further aspect of the invention, there is provided the use of a compound of formula I, or a pharmaceutically acceptable salt thereof in the manufacture of a medicament for use in the production of an antiangiogenic and/or vascular permeability reducing effect in a mammalian animal such as a human being.

According to a further feature of the invention there is provided a method for producing an antiangiogenic and/or vascular permeability reducing effect in a mammalian animal, such as a human being, in need of such treatment which comprises administering to said animal an effective amount of a compound of formula I or a pharmaceutically acceptable salt thereof as defined herein before.

The antiproliferative, antiangiogenic and/or vascular permeability reducing treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines like 5-fluorouracil, purine and adenosine analogues, cytosine arabinoside); Intercalating antitumour antibiotics (for example, anthracyclines like doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids such as vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins such as etoposide and teniposide, amsacrine, topotecan); cell cycle inhibitors (for example, flavopyridols); biological response modifiers and proteasome inhibitors such as Velcade® (bortezomib).

As stated above, the formula I compounds of the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, obesity, acute and chronic nephropathies, atheroma, arterial restenosis, autoimmune diseases, acute inflammation and ocular diseases associated with retinal vessel proliferation such as diabetic retinopathy.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as VEGFR-2.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds may be administered in a dosage range of about 0.05 to 800 mg/kg/day, preferably less than 500 mg/kg/day, in a single dose or in 2 to 4 divided doses.

Biological Assays

| VEGFR-2 and FGFR-1 Kinase assays: | | |
|---|---|---|
| Reagents | Final Concentration | |
| Stock Solution | VEGFR-2 | FGFR-1 |
| Tris pH 7.0 | 20 mM | 20 mM |
| BSA 10 mg/ml | 25 µg/ml | 25 µg/ml |
| MnCl$_2$ (1 M) | 1.5 mM | 0.5 mM |
| MgCl$_2$ (1 M) | — | 0.5 mM |
| DTT(1 M) | 0.5 mM | 0.5 mM |
| Enzyme Stock in 10% glycerol (1 mg/ml) | 5 ng/rxn | 20 ng/rxn |
| Polyglu/tyr (10 mg/ml) | 75 µg/ml | 30 µg/ml |
| ATP (1 mM) | 2.5 µM | 1.0 µM |
| γ-ATP (10 µCi/µl) | 0.5 µCi/ml | 0.5 µCi |

Incubation mixtures employed for VEGFR-2 or FGFR-1 assay contain the synthetic substrate polyGlu:Tyr, (4:1), ATP, ATP-γ-$^{33}$P and buffer containing Mn$^{++}$ and/or Mg$^{++}$, DTT, BSA, and Tris buffer. The reaction is initiated by addition of enzyme and after 60 minutes is terminated by the addition of TCA to 30%. Inhibitors are brought to 10 mM in 100% DMSO. Assays are prepared in a 96 well format. Compounds are diluted 1:500 in 100% DMSO and then 1:10 in water for a final DMSO concentration of 10%. 10 µL are added to rows B–H in a 96 well format of 10% DMSO. 20 µl of compound is added to row A at a concentration 5 fold higher than running conditions. Ten µL are transferred to each row with 10 pippetting phases for mixing, and at row F 10 µL are discarded. Row G is a control with no compound and row H is no compound and no enzyme control. Enzyme and substrate are delivered using a Tomtec Quadra station.

Plates are covered with sticky plate tops, incubated at 27° C. for 60 minutes, and then acid precipitated with TCA for 20 minutes on ice. The precipitate is transferred to UniFilter-96, GF/C microplates using either a Tomtec or Packard FilterMate harvester. Activity is determined by quantitating the incorporated radioactivity using a Packard TopCount Microplate Scintillation Counter following the addition of Microscint-20 cocktail into each dried well of the UniFilter microplates.

The instant compounds inhibit VEGFR-2 and FGFR-1 kinases with IC$_{50}$ values between 0.01 to 10 µM. Preferred compounds have IC$_{50}$ values less than 0.3 µM.

These compounds are selective against VEGFR-2 and FGFR-1 kinase enzymes. They have minimum activity against CDK-2 kinase and LCK and Src kinases. Activity against these kinases is >1 µM.

Methods of Preparation

Certain compounds of formula I may be prepared according to the following schemes and the knowledge of one skilled in the art.

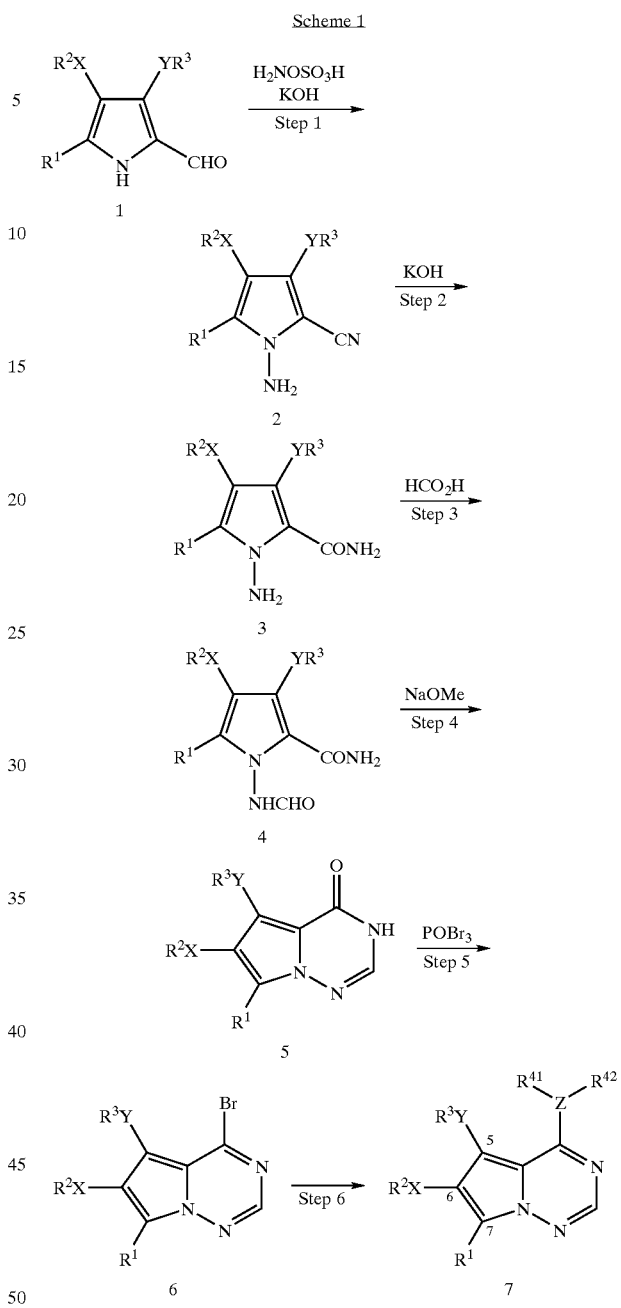

Step 1

The first step is accomplished by the reaction of an optionally substituted 2-formylpyrrole (product 1) with an aminating reagent, such as hydroxylamine-O-sulfonic acid, in an aqueous solvent at RT, followed by treatment under cooling with a base such as potassium hydroxide (KOH). Compounds 1 are obtained from substituted pyrroles by formylation, for example by reaction with phosphorus oxychloride and dimethyl formamide (dimethyl form amide). A methylpyrrole is obtained by reduction of a formylpyrrole, for example by reaction with LiAlH$_4$.

Step 2

The product 2 is reacted with an aqueous base such as KOH at RT to form the product 3 of Scheme 1.

Step 3

The compound 3 is reacted with an acylating agent, such as formic acid, in an aqueous solvent, to form the product 4 of Scheme 1.

Step 4

The compound 4 is cyclized with a base such as sodium methoxide in MeOH with heating to form the product 5 of Scheme 1.

Step 5

The compound 5 is halogenated, for example, with phosphorus oxybromide at elevated temperature, to form the product 6 of Scheme 1.

Step 6

The compound 6 is reacted with an amine such as an aniline in an organic solvent, such as acetonitrile, to form the product 7 of Scheme 1.

The compound 7 of Scheme 1 where $R_1$ is halogen, is prepared from the compound 7 of Scheme 1 where $R_1$ is hydrogen, by reaction with a halogenating agent such as bromine in a suitable solvent such as acetic acid.

Scheme 2

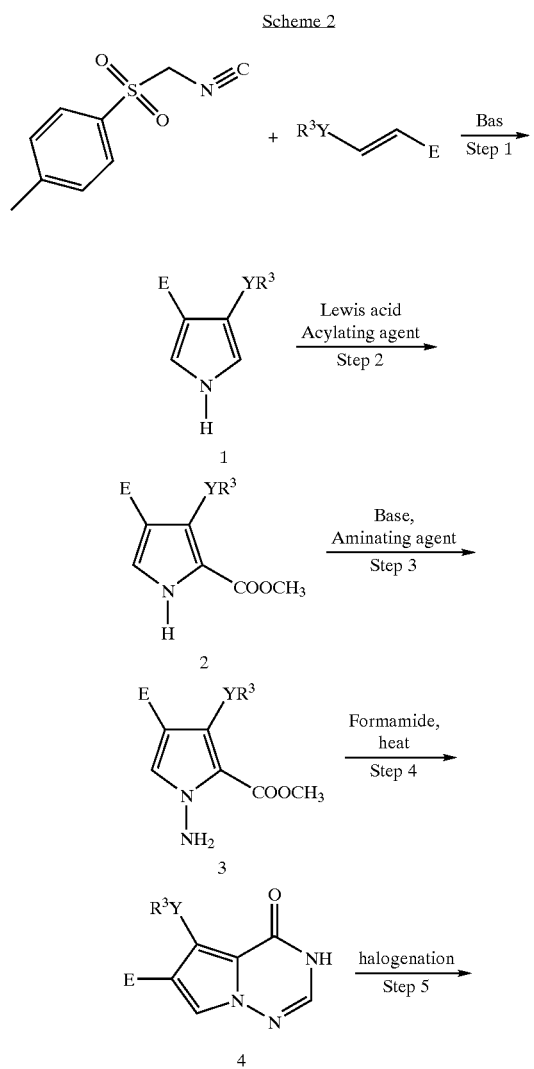

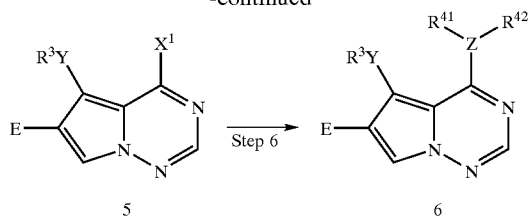

E = electron withdrawing group such as ester or nitro or ketone
$X^1$ = halogen

Step 1

An anion of tosylmethyl isocyanide (TosMIC) is reacted with a Michael acceptor such as ethyl crotonate to obtain disubstituted pyrrole 1. An anion of TosMIC is made by treating a solution of it in DMSO with a base such as NaH at RT, or by treating a solution of it in THF with lithium hexamethyldisilazane at −78° C.

Step 2

Treatment of pyrrole 1 with an acylating agent such as trichloroacetyl chloride in the presence of a Lewis acid, such as aluminum chloride, at from RT to 50° C. followed by treatment with sodium methoxide affords trisubstituted pyrrole 2. Alternatively, following the published procedure of (M. Suzuki, M. Miyoshi, K. Matsumoto, *J. Org. Chem.* 1974, 39, 1980), compound 2 is obtained by warming an aldehyde, such as acetaldehyde, with 2 equivalents of ethyl isocyanoacetate in the presence of a base, such as DBU, in an organic solvent, such as tetrahydrofuran.

Step 3

Pyrrole 2 is aminated by an aminating reagent, such as diphenyl phosphoryl hydroxylamine, in the presence of a base, such as sodium hydride, at RT in organic solvent, such as DMF.

Step 4

N-Aminated pyrrole 3 upon heating at from 120 to 195° C. with formamide undergoes cyclization to afford 1,2,4-triazine compound 4.

Step 5

Compound 4 upon treatment with a halogenating agent, such as phosphorous oxybromide at from 60 to 115° C., in the presence or absence of a co-solvent such as DCE, affords compound 5.

Step 6

Compound 5 is reacted with amines, such as anilines in an organic solvent, such as DMF, to obtain compound 6.

Scheme 3

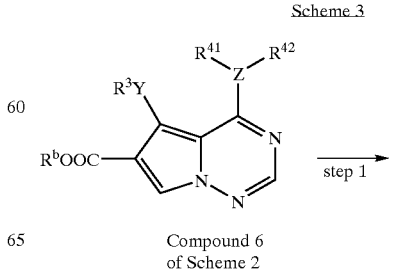

Compound 6
of Scheme 2

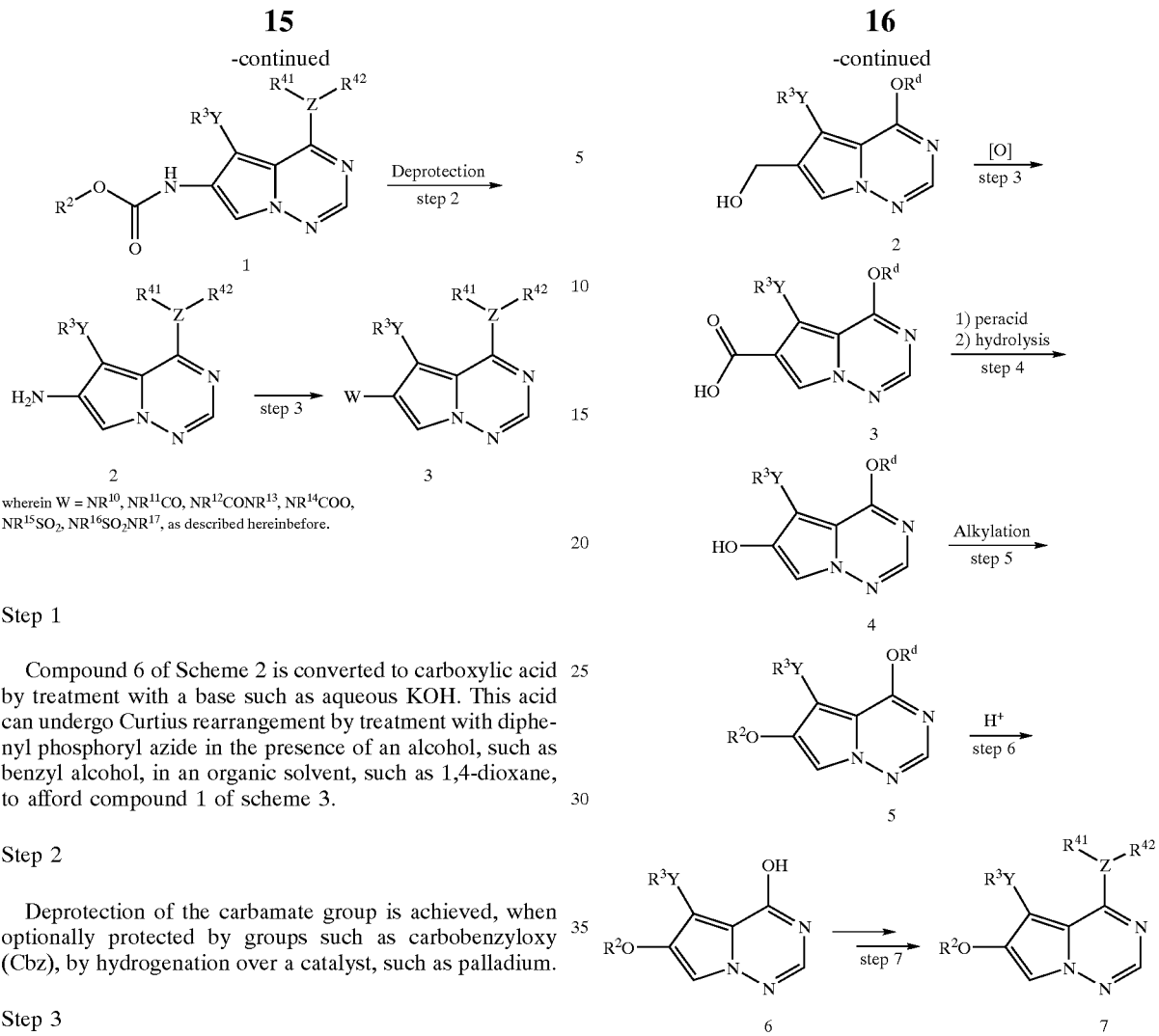

wherein W = NR$^{10}$, NR$^{11}$CO, NR$^{12}$CONR$^{13}$, NR$^{14}$COO, NR$^{15}$SO$_2$, NR$^{16}$SO$_2$NR$^{17}$, as described hereinbefore.

Step 1

Compound 6 of Scheme 2 is converted to carboxylic acid by treatment with a base such as aqueous KOH. This acid can undergo Curtius rearrangement by treatment with diphenyl phosphoryl azide in the presence of an alcohol, such as benzyl alcohol, in an organic solvent, such as 1,4-dioxane, to afford compound 1 of scheme 3.

Step 2

Deprotection of the carbamate group is achieved, when optionally protected by groups such as carbobenzyloxy (Cbz), by hydrogenation over a catalyst, such as palladium.

Step 3

The amino group of compound 2 is acylated, for example, by treatment with a carboxylic acid in the presence of a coupling agent such as DCC, or is sulfonylated, for example, by treatment with a sulfonyl chloride. Alternatively, the amino group of compound 2 is alkylated with alkyl halides or undergoes reductive amination with aldehydes in the presence of a reducing agent, such as sodium cyanoborohydride.

X$^1$ = halogen
R$^d$ = R$^e$ = R$^6$ described hereinabove

Step 1
Compound 5 of Scheme 2 is converted to an ether (etherified) at the 4-position, for example, by treatment with phenoxide or methoxide anion.

Step 2
Reduction of compound 1 of scheme 4 with a reducing agent, such as diisobutylaluminum hydride (DIBAL), in an organic solvent, such as toluene, affords the alcohol compound 2.

Step 3
Oxidation of the alcohol is achieved by treatment of compound 2, for example, with manganese dioxide (MnO$_2$) at an elevated temperature in an organic solvent, such as toluene.

Step 4
Treatment of compound 3 with an oxidant, such as m-chloroperbenzoic acid (m-CPBA), in an organic solvent, such as dichloromethane (DCM), followed by aqueous hydrolysis with a base, such as potassium bicarbonate, affords the hydroxyl compound 4 of scheme 4.

Step 5
Alkylation of the phenol group in compound 4 with an agent, such as iodomethane, in the presence of a base, such as NaH, at from RT to 100° C., affords compound 5.

Step 6

Hydrolysis of compound 5 is achieved by treatment with an acid, such as aqueous HCl, at an elevated temperature, to afford compound 6.

Step 7

Compound 6 is converted to compound 7 using procedures analogous to those described in Scheme 2.

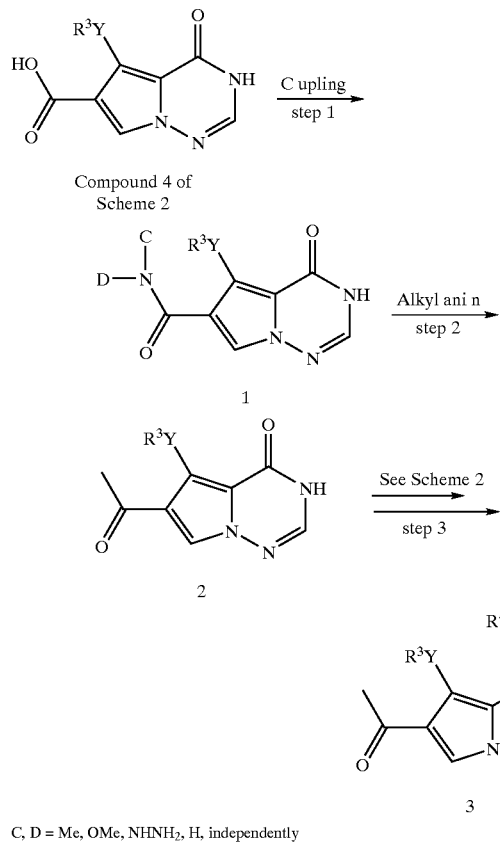

C, D = Me, OMe, NHNH$_2$, H, independently

Step 1

Compound 4 of Scheme 2 in which E=carboxylic acid, could be treated with an amine like ammonia or N,O-dimethylhydroxyl amine or substituted hydrazine in the presence of a coupling agent, such as dicyclohexylcarbodiimide (DCC) to obtain compound 1 as an amide or a hydrazide.

Step 2

When the amine used in Step 1 is N,O-dimethylhydroxyl amine, the resulting compound could be treated with an alkylating agent such as methyllithium, to obtain compound 2.

Step 3

Compound 2 then could be converted to compound 3 as described before in scheme 2.

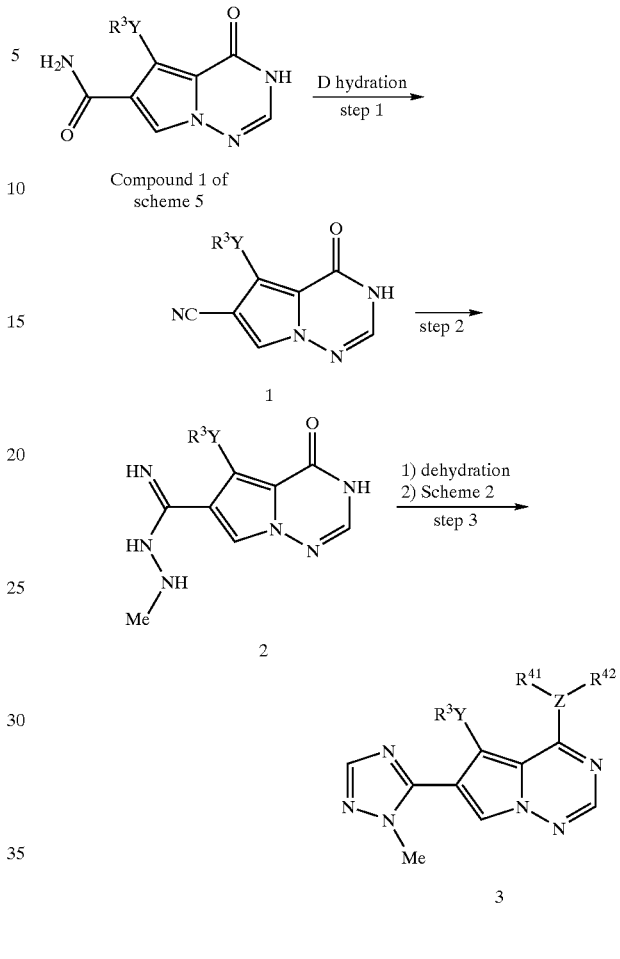

Step 1

When the amine used in Step 1 of Scheme 5 is ammonia, the resulting compound could be treated with a dehydrating agent such as phosphorous oxychloride, to obtain compound 1.

Step 2

The compound 1 could then be treated with a strong acid such as sulfuric acid in an alcohol such as ethanol to obtain an imidate which then could be treated with substituted hydrazine such as methylhydrazine to obtain compound 2.

Step 3

The compound 2 could then be treated with a dehydrating agent such as phosphorous oxychloride, to obtain an intermediate chloroimidate which when treated further with an appropriate aniline could afford compound 3 as described in scheme 2.

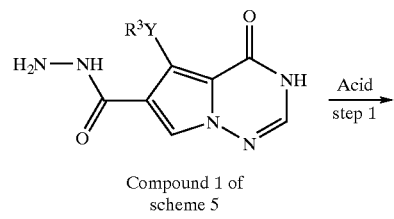

19

-continued

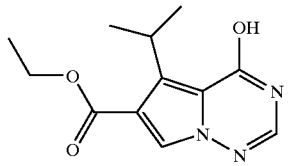

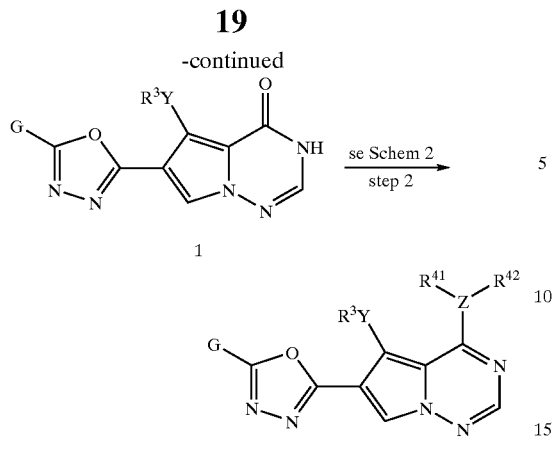

G = substituted methyl or methylene or
substituted nitroen or substituted sulfur etc.

Step 1

When the amine used in Step 1 of Scheme 5 is hydrazine, the resulting compound could be treated with an acid such as difluoroacetic acid in the presence of a dehydrating agent such as phosphorous oxychloride, or substituted acetimidic ester or phosgene imidinium chloride to obtain compound 1.

Step 2

The compound 1 could be then converted to compound 2 as described before in Scheme 2.

EXAMPLES

In addition, other compounds of formula I may be prepared using procedures generally known to those skilled in the art. In particular, the following examples provide additional methods for preparing compounds of this invention.

The invention will now be further described by the following working examples, which are preferred embodiments of the invention. These examples are illustrative rather than limiting, and it is to be understood that there may be other embodiments that fall within the spirit and scope of the invention as defined by the claims appended hereto.

All temperatures are in degrees Celsius (° C.) unless otherwise indicated. Reverse Phase (RP) HPLC purifications were done on C18 reverse phase (RP) columns using water methanol mixtures and 0.1% TFA as buffer solution. All the synthesized compounds were characterized by at least proton NMR and LC/MS. During work up of reactions, the organic extract was dried over magnesium sulfate (MgSO$_4$), unless mentioned otherwise. Following abbreviations are used for the commonly used reagents. NMM; N-methylmorpholine, DIBALH; diisobutylaluminum hydride, BOP reagent; benzotriazol-1-yloxy-tris(trimethylamino)phosphonium hexafluorophosphate, DCE; dichloroethane, K$_2$CO$_3$; potassium carbonate, KOH; potassium hydroxide, DCC; dicyclohexyl carbodiimide, EDCI; 1-(dimethylaminopropyl)-3-ethylcabodiimide hydrochloride, RT; room temperature, HOBt; hydroxybenzotriazole, DCM; dichloroethane, CbzCl; chlorobenzoyl chloride, NaHCO$_3$; sodium bicarbonate, HCl; hydrochloric acid, TFA; trifluoroacetic acid, NH$_4$Cl; ammonium chloride, DIPEA; diisopropylamine, Et$_3$N; triethylamine, RT; room temperature.

20

Example 1

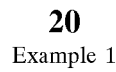

5-(1-Methylethyl)pyrrolo[2,1-f][1,2,4]triazin-4(3H)-one-6-carboxylic acid ethyl ester A) Ethyl isocyanoacetate (80 g, 0.71 mol) was dissolved in 1 L of dry tetrahydrofuran under nitrogen and 1,8-diazabicyclo[5.4.0]undec-7-ene (107.7 g, 0.71 mol) was added to the solution. A solution of isobutyraldehyde (29.7 g, 0.41 moles) in 1.5 L of dry tetrahydrofuran was added dropwise at room temperature over 3 hours. The mixture was then stirred at room temperature for 16 h. The reaction mixture was concentrated under vacuum to a brown oil. The concentrate was partitioned between 1.2 L of ethyl acetate and 0.5 L of water. The organic layer was then washed with 0.4 L of 0.1 N hydrochloric acid followed by 0.3 L of saturated sodium bicarbonate solution and then 0.3 L of saturated brine. The organic layer was dried (sodium sulfate), filtered and concentrated under vacuum to a brown oil. The residue was dissolved in toluene and added to a 1600 ml (~800 g) column of silica gel wet with hexane. Product was eluted at 15 PSI nitrogen pressure first with 4.8 L of hexane followed by 5 L of 20% ethyl acetate in hexane. Eluent containing product by TLC analysis was combined and concentrated under vacuum to a yellow oil. The concentrate was pumped dry under high vacuum giving product A, 3-(1-methylethyl)pyrrole-2,4-dicarboxylic acid diethyl ester (54 g, 60% yield) of yellow oil that solidified on standing at room temperature. TLC silica gel:

R$_f$=0.2, hexane/ethyl acetate (4/1) uv visualization and PMA stain. $^1$H NMR; (CDCl$_3$) δ 1.2–1.5 (m, 12H), 4.2–4.3 (m, 1H), 4.3–4.3 (m, 4H), 7.5 (d, 1H).

B) To a suspension of NaH (13.9 g, 34 mmol, 60% in oil) in DMF (0.36 L) at 0° C. was added a solution of compound A (75 g, 29 mmol) in DMF (0.4 L). After stirring for 45 min., 2,4-dinitrohydroxylamine was added in small portions. After the addition was complete, the cold bath was removed and the mixture was allowed to warm to room temperature. After 2 h., the reaction mixture was poured into water and extracted with ethyl acetate. The organic layer was washed with saturated sodium bicarbonate, 10% lithium chloride (LiCl) and brine, then dried (Na$_2$SO$_4$) and concentrated. The residue was purified to afford the desired compound 1-amino-3-(1-methylethyl)pyrrole-2,4-dicarboxylic acid dimethyl ester, as an oil (81 g) at 80% purity which was used without further purification.

C) Compound B (81 g crude, 0.029 mol) was mixed with formamide (0.5 L) and heated to 160° C. After 8 h., the mixture was allowed to cool to RT and stirred for 2 days. It was then diluted with water (4L) and the mixture was extracted with ethyl acetate. The organic layer was concentrated, toluene was added to the residue and concentrated again. The brown solid was triturated with ether and dried under high vacuum to afford 5-(1-methylethyl)pyrrolo[2,1-f][1,2,4]triazin-4(3H)-one-6-carboxylic acid ethyl ester, as a light brown solid (45 g, 62%). LC/MS; (M+H)$^+$= 250.1

Example 2

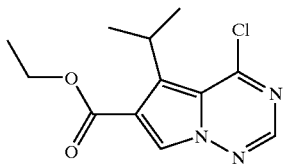

4-Chloro-[2,1-f][1,2,4]triazin-5-(1-methylethyl)pyrrolo-6-carboxylic acid ethyl ester A solution of Example 1 (1 g) in phosphorous oxychloride (5 ml) was heated at 110° C. for 3 h. The mixture was cooled and concentrated in vacuo to afford the title compound (90% yield) as an oil. LC/MS; (M+H)$^+$=268.7. The compound was used without further purification.

Example 3

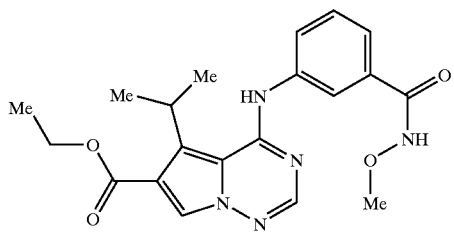

4-[[3-[(Methoxyamino)carbonyl]phenyl]amino]-5-(1-methylethyl)pyrrolo[2,1-f][1,2,4]triazine-6-carboxylic acid ethyl ester To a solution of chloroimidate from Example 2 (19 mg, 0.071 mmol) in DMF (1 mL) was added 3-methoxyaminocarbonyl aniline (18 mg, 0.11 mmol) and the mixture was stirred at room temperature for 3 h. The mixture was purified by HPLC using reverse phase chromatography column eluting with a mixture of methanol and water containing 0.1% TFA. The desired fractions were collected and concentrated. The residue was treated with methanol and 1 N HCl and concentrated to afford the title compound as a solid (20 mg, 65%) of product. MS: (M+H)$^+$=398.3.

Examples 4 to 8

Examples 4 to 8 were prepared using a procedure similar to that described for the preparation of Example 3 using the appropriate aniline. The general structure of the compounds prepared in Examples 4–8 is shown below, wherein the R substituent is listed in Table I for each example.

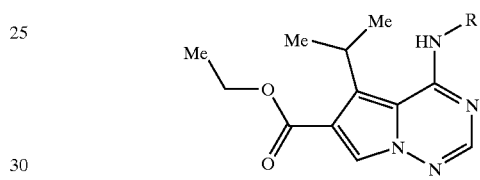

TABLE I

| Example # | R | Name | LC/MS: (M + H)$^+$ |
|---|---|---|---|
| 4 | ![F, benzamide with HN-O-Me] | 4-[[2-Fluoro-5-[(methoxyamino)carbonyl]phenyl]amino]-5-(1-methylethyl)pyrrolo[2,1-f][1,2,4]triazine-6-carboxylic acid ethyl ester | 416.4 |
| 5 | ![F, Me, benzamide with HN-O-Me] | 4-[[2-Fluoro-5-[(methoxyamino)carbonyl]-4-methylphenyl]amino]-5-(1-methylethyl)pyrrolo[2,1-f][1,2,4]triazine-6-carboxylic acid ethyl ester | 430.5 |
| 6 | ![Me, benzamide with HN-O-Me] | 4-[[3-[(Methoxyamino)carbonyl]-4-methylphenyl]amino]-5-(1-methylethyl)pyrrolo[2,1,-f][1,2,4]triazine-6-carboxylic acid ethyl ester | 411.1 |
| 7 | ![F, benzamide with HN-O-Me] | 4-[[4-Fluoro-3-[(methoxyamino)carbonyl]phenyl]amino]-5-(1-methylethyl)pyrrolo[2,1-f][1,2,4]triazine-6-carboxylic acid ethyl ester | 416.3 |

TABLE I-continued

| Example # | R | Name | LC/MS: (M + H)+ |
|---|---|---|---|
| 8 | 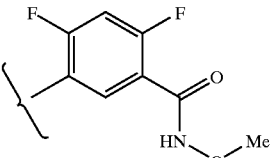 | 4-[[2,4-Difluoro-5-[(methoxyamino)carbonyl]phenyl]amino]-5-(1-methylethyl)pyrrolo[2,1-f][1,2,4]triazine-6-carboxylic acid ethyl ester | 433.2 |

Certain anilines used in the preparation of the above examples were prepared as shown in Examples 9, 10, 17 and 21.

The following compounds were prepared by a procedure similar to that described for the preparation of Example 3 using appropriate anilines.

Example 9

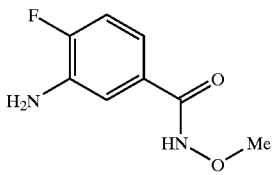

3-Amino-4-fluoro-N-methoxybenzamide

A) To a solution of 4-fluoro-3-nitrobenzoic acid (20 g, 0.108 mol) in dichloromethane (0.5 L) were added dimethyl formamide (0.1 mL) and oxalyl chloride (47 mL, 0.54 mol) over 20 min. After 1 h, the mixture was concentrated in vacuo to afford the acid chloride, 4-fluoro-3-nitro-benzoyl chloride (23.32 g) as yellow oil which was used without further purification.

B) To a solution of compound A (23.3 g, 0.11 mol) in dichloromethane (300 mL) were added triethylamine (45 mL, 0.32 mol) followed by hydroxyl amine hydrochloride (13.88 g, 0.166 mol) in several portions. After 18 h, the mixture was concentrated and the residue was partitioned between ethyl acetate and water. The organic layer was separated, washed successively with saturated NaHCO$_3$, brine, dried, and concentrated to afford the 4-fluoro-N-methoxy-5-nitrobenzamide (22.1 g, 95% two steps overall). LC/MS (ESI); (M−H)−=213−.

C) To a solution of compound B (5 g, 23.55 mmol) in methanol was added 10% Pd/C and the mixture was stirred under hydrogen at 1 atmospheric pressure. After 4 h, the hydrogen was removed, the mixture was filtered and the filtrate was concentrated in vacuo. The residue was triturated with dichloromethane to afford 5-amino-4-fluoro-N-methoxybenzamide as white solid (16.68 g, 73%). LC/MS; (M+H)+=185.1.

Example 10

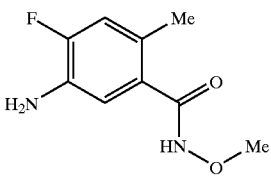

5-amino-2-methyl-4-fluoro-N-methoxybenzamide

A) To a solution of 2-methyl-5-nitro-4-fluorobenzoic acid (1.77 g, 8.9 mmol, for preparation see Coll. Czech. Chem. Commun. 1977, 42, 2001) in ethanol (15 mL) was added 10% Pd/C (50 mg) and the mixture was subjected to hydrogenation under 30 psi of pressure. After 3 h, hydrogen was removed and the mixture was filtered and the filtrate was concentrated in vacuo to afford 2-methyl-5-amino-4-fluorobenzoic acid (1.45 g, 97%). LC/MS; (M+H)+=170.

B) To a solution of compound A (0.85 g, 5 mmol) in tetrahydrofuran (10 mL) was added BOC anhydride (1.38 g) and the mixture was refluxed for 1 h. More BOC anhydride (1 g) was added. After 1 h, the mixture was concentrated and the residue was washed with 0.5 N HCl and filtered, dried in vacuo to afford the N-BOC protected derivative of 2-methyl-5-amino-4-fluorobenzoic acid (820 mg, 60%). LC/MS; (M+H)+=270.

C) To a solution of compound B (820 mg, 3 mmol) in dimethyl formamide (10 mL) were added EDCI (700 mg, 3.6 mmol), HOBt (460 mg, 3 mmol), methoxylamine hydrochloride (370 mg, 3.6 mmol) and triethylamine (0.9 mL). After stirring for 1 h at RT, the mixture was diluted with ethyl acetate and washed with water, dried and concentrated. The solid obtained was dissolved in dichloromethane (2.5 mL) and TFA (2.5 mL) was added. After 2 h, the mixture was concentrated, the residue was dissolved in ethyl acetate and washed with saturated NaHCO$_3$ to afford 5-amino-2-methyl-4-fluoro-N-methoxybenzamide (520 mg). LC/MS; (M+H)+=199.2.

Example 11

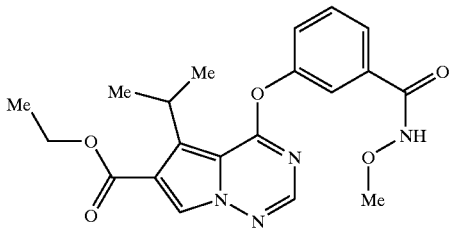

4-[3-[(Methoxyamino)carbonyl]phenoxy]-5-(1-methylethyl)pyrrolo[2,1-f][1,2,4]triazine-6-carboxylic acid, ethyl ester To a solution of Example 2 (20 mg, 0.075 mmol) in dimethyl formamide at RT were added 3-[(methoxyamino)carbonyl]phenol (25 mg, 0.15 mmol) and potassium carbonate (21 mg, 0.15 mmol) and the mixture was stirred at RT overnight. The mixture was filtered, the solids were washed with methanol and the filtrate was concentrated. The residue was purified by reverse phase preparative HPLC to afford the title compound (42 mg, 57%) as a solid. MS: $(M+H)^+=399.2$.

Example 12

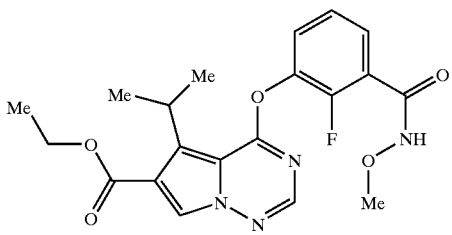

4-[2-Fluoro-3-[(methoxyamino)carbonyl]phenoxy]-5-(1-methylethyl)pyrrolo[2,1-f][1,2,4]triazine-6-carboxylic acid, ethyl ester A) To a solution of 2-fluoro-3-methoxy carboxylic acid (510 mg, 3 mmol) in DCM was added 1M solution of boron tribromide (30 mL, 30 mmol) at 0° C. for 5 h, followed by stirring at RT for 72 h. A precipitate formed which was filtered and dried to afford the desired product, 2-fluoro-3-carboxyphenol (440 mg, 94%). LC/MS; $(M+H)^+=157.2$ B) To a solution of Example 2 (56 mg, 0.26 mmol) in acetonitrile were added 2-fluoro-3-carboxyphenol (80 mg, 0.51 mmol) and triethylamine (0.071 mL, 0.51 mmol) at RT. After 18 h, the mixture was concentrated and purified by reverse phase preparative HPLC. The appropriate fractions were collected and concentrated to afford the desired product (15 mg, 15%). LC/MS; $(M+H)^+=388.3$ C) To a solution of 4-[2-fluoro-3-carboxyphenoxy]-5-(1-methylethyl)pyrrolo[2,1-f][1,2,4]triazine-6-carboxylic acid, ethyl ester (14 mg, 0.036 mmol) in dimethyl formamide at RT were added EDCI (14 mg, 0.07 mmol), DIPEA (20 μL, 0.11 mmol), HOBt (9.7 mg, 0.07 mmol), and methoxylamine hydrochloride (6 mg, 0.07 mmol). After stirring overnight, HPLC analysis revealed that only 10% product was formed. BOP reagent (0.1 mmol) was added. After 6 h, all the starting material was consumed. The mixture was purified by reverse phase preparative HPLC to afford the desired product (14 mg, 93%). LC/MS: $(M+H)^+=417$.

Example 13

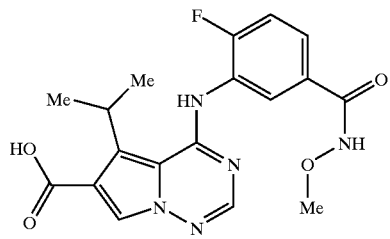

4-[[2-Fluoro-5-[(methoxyamino)carbonyl]phenyl]amino]-5-(1-methylethyl)pyrrolo[2,1-f][1,2,4]triazine-6-carboxylic acid Example 4 (0.41 g, 0.99 mmol) was treated with a mixture of 1N NaOH/tetrahydrofuran (5 mL each) at 70° C. for 36 h. The reaction mixture was cooled to ambient temperature and washed with ethyl acetate. The aqueous layer was acidified to pH 4 and extracted with ethyl acetate and dichloromethane. The combined organic layer was dried, concentrated and triturated with ether to afford the title compound (95%). MS (ESI): $(M+H)^+=388.1$. The compound was used without further purification.

Example 14

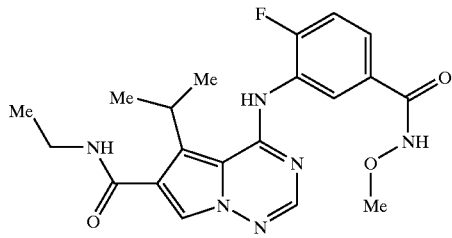

N-Ethyl-4-[[2-fluoro-5-[(methoxyamino)carbonyl]phenyl]amino]-5-(1-methylethyl)pyrrolo[2,1-f][1,2,4]triazine-6-carboxamide A mixture of Example 13 (20 mg, 0.052 mmol), ethylamine hydrochloride (6 mg, 0.08 mmol), BOP reagent (34 mg, 0.08 mmol), and N-methyl morpholine (0.012 mL, 0.1 mmol) in dimethyl formamide (0.5 mL) was stirred at RT for 18 h. The mixture was purified by reverse phase HPLC. The appropriate fractions were concentrated and the residue was converted to the HCl salt to obtain the desired product as a white solid (11 mg, 50%). LC/MS; $(M+H)^+=415.2$

Examples 15 and 16

Examples 15 and 16 were prepared from Example 13 by a procedure similar to that described for Example 14 using the appropriate amine.

Example 15

N-[2-(Dimethylamino)ethyl]-4-[[2-fluoro-5-[(methoxyamino)carbonyl]phenyl]amino]-5-(1-methylethyl)pyrrolo[2,1-f][1,2,4]triazine-6-carboxamide

LC/MS; $(M+H)^+=458.3$

Example 16

4-[[2-Fluoro-5-[(methoxyamino)carbonyl]phenyl]amino]-N-(2-hydroxyethyl)-5-(1-methylethyl)pyrrolo[2,1-f][1,2,4]triazine-6-carboxamide

LC/MS; $(M+H)^+=431.2$.

Example 17

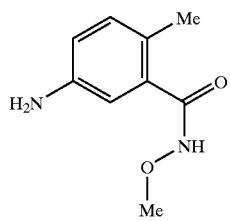

5-amino-2-methyl-N-methoxycarboxamide

A) To a solution of compound of 2-methyl-5-nitrobenzoic acid (0.45 g, 2.5 mmol) in tetrahydrofuran (25 mL) at RT were added EDCI (0.96 g, 5 mmol), HOBt (0.68 g, 5 mmol), methoxylamine hydrochloride (0.31 g, 3.75 mmol) followed by DIPEA (0.44 mL, 2.5 mmol). After 6 h, the mixture was diluted with ethyl acetate and washed successively with saturated $NaHCO_3$, 1N HCl solution, and brine. The organic layer was dried, concentrated and the residue was purified by flash column chromatography eluting with 0 to 2% methanol in chloroform to afford 2-methyl-5-nitro-N-methoxycarboxamide (310 mg, 60%). LC/MS; $(M+H)^+$=211.1.

B) To a solution of compound A (304 mg, 1.46 mmol) in ethanol (3 mL) at RT was added $SnCl_2.H_2O$ (1.38 g, 7.3 mmol) followed by concentrated HCl (3 mL). The mixture was heated to 50° C. for 10 min. The mixture was cooled to RT, concentrated; the residue was dissolved in ethyl acetate, and $NaHCO_3$ solution was added dropwise to neutralize the mixture. The organic layer was separated, dried, and concentrated to afford 5-amino-2-methyl-N-methoxycarboxamide (196 mg, 75%). LC/MS; $(M+H)^+$=181.1.

Example 18

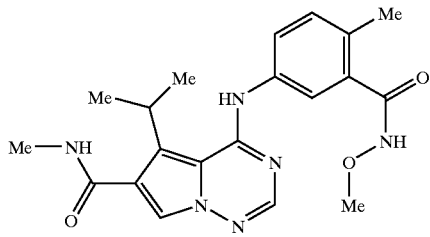

4-[[3-[(Methoxyamino)carbonyl]-4-methylphenyl]amino]-N-methyl-5-(1-methylethyl)pyrrolo[2,1-f][1,2,4]triazine-6-carboxamide A) A solution of Example 6 (0.16 g, 0.34 mmol) in tetrahydrofuran/methanol/water (3 mL/1 mL/1 mL) was treated with lithium hydroxide (33 mg, 0.7 mmol) and heated to 55° C. for 18 h. Additional lithium hydroxide (5.6 mmol) were added and heated for additional 6 h. The mixture was cooled and 1 N HCl was added and pH of the solution was adjusted between 5 and 6. The mixture was concentrated, extracted with ethyl acetate, dried ($Na_2SO_4$), concentrated and the residue was purified by flash column chromatography on silica gel eluting with 5% methanol in chloroform to afford pure acid, 5-(methylethyl)-4-(3-methoxycarbamoyl-4-methyl-phenylamino)-pyrrolo[2,1-f][1,2,4]triazine-6-carboxylic acid (63 mg, 43%). LC/MS; $(M+H)^+$=384.2.

B) To a solution of compound A (31 mg, 0.08 mmol) in dimethyl formamide (1.6 mL) were added BOP reagent (53 mg. 0.12 mmol) and a 2M solution of methyl amine in methanol. After 2 h, the mixture was concentrated and purified by reverse phase preparative HPLC. The appropriate fractions were collected, concentrated and the compound was converted to the HCl salt by treatment with 1 N aqueous HCl to afford the salt of the title compound (19 mg, 60%). LC/MS; $(M+H)^+$=397.

Example 19

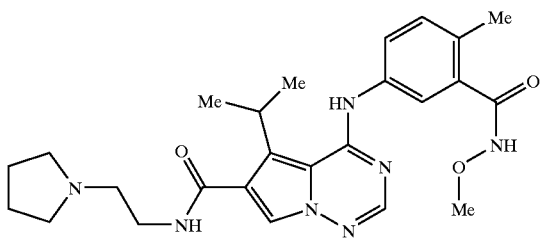

4-[[3-[(Methoxyamino)carbonyl]-4-methylphenyl]amino]-5-(1-methylethyl)-N-[2-(1-pyrrolidinyl)ethyl]pyrrolo[2,1-f][1,2,4]triazine-6-carboxamide Example 19 was prepared from compound A of Example 18 and 2-pyrrolidin-1-yl-ethylamine by a method analogous to the preparation of Example 18 in similar yields LC/MS; $(M+H)^+$=480.4.

Example 20

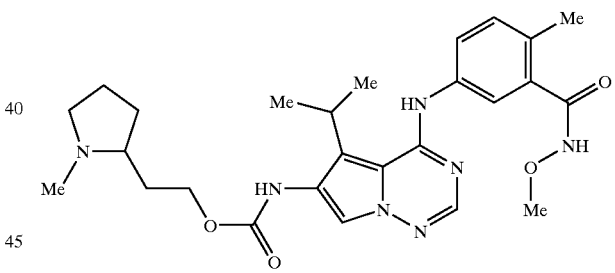

[4-[[3-[(Methoxyamino)carbonyl]-4-methylphenyl]amino]-5-(1-methylethyl)pyrrolo[2,1-f][1,2,4]triazin-6-yl]carbamic acid 2-(1-methyl-2-pyrrolidinyl)ethyl ester To solution of compound A of Example 18 (63 mg, 0.16 mmol) in 1,4-dioxane (1.7 mL) at RT were added 4A sieves, triethylamine (0.91 mmol) and diphenylphosphoryl azide (0.41 mmol). The resulting mixture was warmed to 50° C. for 2 h, then to 80° C. and 2-(1-methylpyrrolidin-2-yl)-ethanol (0.82 mmol) was added. After 2 h, the mixture was cooled RT, filtered and water was added. The mixture was purified by reverse phase preparative HPLC. The appropriate fractions were collected and concentrated. The residue was further purified by silica gel column chromatography eluting with 1% $NH_4OH$, 5% methanol in dichloromethane to afford the title compound (17 mg, 20%). LC/MS; $(M+H)^+$=510.3

Example 21

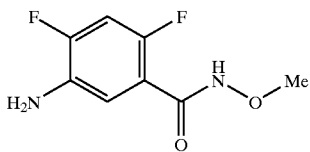

5-Amino-2,4-difluoro-N-methoxybenzamide

A) To a suspension of 2,4-difluorobenzoic acid (9.985 g, 63.2 mmol) in concentrated sulfuric acid (30 mL) at 0° C. was added fuming nitric acid (30 mL) over 30 min. The mixture was allowed to warm to RT and stirred for additional 16 h. The homogeneous mixture was poured over ice and extracted with ethyl acetate. The organic extract was washed with water, dried and concentrated in vacuo to afford 2,4-difluoro-5-nitrobenzoic acid (12.56 gm, 98%) as pale yellow solid.

B) To a solution of the above compound A (0.998 g, 4.91 mmol) in ethanol (50 mL) was added 10% palladium on charcoal (107 mg) and the mixture was subjected to hydrogenation at 30 psi. After 2 h, the mixture was degassed, filtered and the filtrate was concentrated in vacuo to afford 2,4-difluoro-5-aminobenzoic acid (0.83 g, 97%) as tan solid. LC/MS (ESI); (M−H)⁻=172.

C) To a solution of the above Compound B (0.2 g, 1.18 mmol) in dimethyl formamide (10 mL) were added O-methylhydroxylamine hydrochloride (0.3 g, 3.6 mmol) and DIPEA (0.83 mL, 4.76 mmol). The mixture was cooled to 0° C. and a solution of BOP reagent (0.79 g, 1.78 mmol) in dimethyl formamide (3 mL) were added. The mixture was allowed to warm to RT and stirred for 60 h. The mixture was poured into water and extracted with ethyl acetate. The organic layer was washed sequentially with saturated sodium bicarbonate, 10% lithium chloride solution, dried and concentrated in vacuo to afford the desired product as a brown solid (0.13 g, 53%). LC/MS; (M+H)⁺=203.2.

Example 22

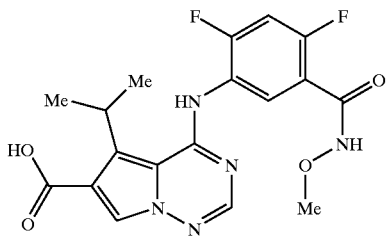

4-[[2,4-Difluoro-5-[(methoxyamino)carbonyl]phenyl]amino]-5-(1-methylethyl)pyrrolo[2,1-f][1,2,4]triazine-6-carboxylic acid Example 8 was hydrolyzed to afford Example 22 using a procedure similar to that for the preparation of compound A of Example 18. LC/MS; (M+H)⁺=406.3

Example 23

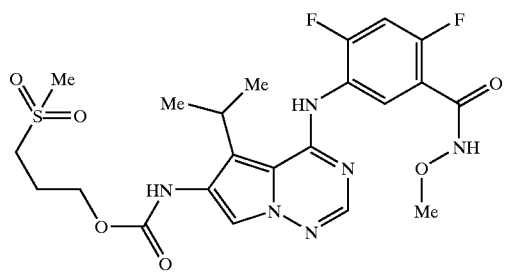

[4-[[2,4-Difluoro-5-[(methoxyamino)carbonyl]phenyl]amino]-5-(1-methylethyl)pyrrolo[2,1-f][1,2,4]triazin-6-yl]carbamic acid 3-(methylsulfonyl)propyl ester A) To a solution of Example 22 (1.11 g, 2.74 mmol) in dioxane (25 mL) was added triethylamine (0.57 mL, 4.1 mmol) followed by diphenylphosphoryl azide (0.77 mL, 3.57 mmol) and the resulting mixture was stirred at 40° C. After 1 h, the mixture was concentrated and the residue was purified by silica gel column chromatography eluting with ethyl acetate in hexanes to afford acyl azide, 4-(2,4-difluoro-5-methoxycarbamoyl-phenylamino)-5-isopropyl-pyrrolo[2,1-f][1,2,4]triazine-6-carbonyl azide (0.95 g, 81%) as pale yellow foam.

B) To a solution of Compound A (1.05 g, 2.44 mmol) in dimethyl formamide (25 mL) at RT was added 3-(methylsulfonyl)propanol (0.75 g, 5.3 mmol). The mixture was stirred at 85° C. for 2 h, cooled and concentrated in vacuo. The residue was dissolved in dichloromethane and concentrated. The solid obtained was then triturated with dichloromethane several times to remove impurities. The resulting solid was treated with HCl in ether to obtain the salt of the title compound (0.9 g, 65%) as an off-white solid. LC/MS; (M+H)⁺=541.3

Examples 24 and 25

Examples 24 and 25 were prepared from Example 22 by using a procedure similar to that for the preparation of Example 23.

Example 24

[4-[[2,4-Difluoro-5-[(methoxyamino)carbonyl]phenyl]amino]-5-(1-methylethyl)pyrrolo[2,1-f][1,2,4]triazin-6-yl]carbamic acid ethyl ester.

LC/MS; (M+H)⁺=449.3.

Example 25

[4-[[2,4-Difluoro-5-[(methoxyamino)carbonyl]phenyl]amino]-5-(1-methylethyl)pyrrolo[2,1-f][1,2,4]triazin-6-yl]carbamic acid 3-(1-piperidinyl)propyl ester

LC/MS; (M+H)⁺=546.5.

Example 26

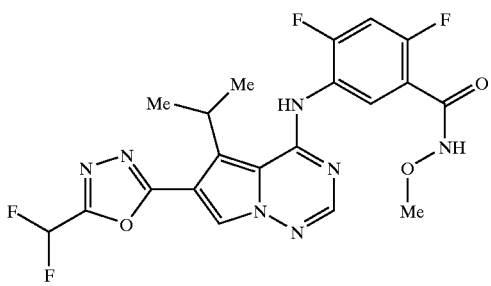

5-[[6-[5-(Difluoromethyl)-1,3,4-oxadiazol-2-yl]-5-(1-methylethyl)pyrrolo[2,1-f][1,2,4]triazin-4-yl]amino]-2,4-difluoro-N-methoxybenzamide A) Example 1 was dissolved in a 4:1 mixture of hydrazine in ethanol and the mixture was heated at 88° C. for 4 h. The mixture was cooled and concentrated in vacuo to afford 5-isopropyl-4-oxo-3,4-dihydropyrrolo[2,1-f][1,2,4]triazine-6-carboxylic acid hydrazide (0.9 g, 95%) as brown solid.

B) Compound A (100 mg, 0.43 mmol) and difluoroacetic acid were added to phosphorous oxychloride (10 mL) and the resulting mixture was heated at 120° C. for 3 h. The reaction mixture was cooled to ambient temperature and concentrated in vacuo. The residue was partitioned between ethyl acetate and saturated NaHCO₃. The organic layer was separated, dried (Na₂SO₄), filtered and concentrated. The resulting oily residue was then dissolved in acetonitrile (5 mL) and 5-amino-2,4-difluoro-N-methoxybenzamide (0.13 g, 0.63 mmol) was added. The mixture was stirred for 18 h. The precipitate that formed was filtered and the solid obtained was washed with acetonitrile and dried in vacuo to afford the title compound (86 mg, 42% overall) as a white solid. LC/MS; (M+H)⁺=480.

Example 27

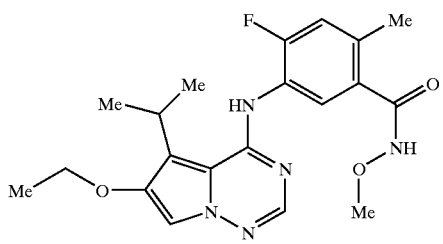

5-[[6-Ethoxy-5-(1-methylethyl)pyrrolo[2,1-f][1,2,4]triazin-4-yl]amino]-4-fluro-N-methoxy-2-methylbenzamide A) To a solution of Example 2 (802 mg, 3 mmol) in methanol (10 mL) at RT was added solid sodium methoxide (350 mg, 6.48 mmol). After 1 h, the mixture was neutralized with 1N HCl, and concentrated in vacuo. The residue was extracted with ethyl acetate three times and the combined organic extracts were washed with brine, dried, and concentrated. The residue was purified by flash column chromatography eluting with ethyl acetate in hexanes (2:1) to afford 4-methoxy-[2,1-f][1,2,4]triazin-5-(1-methyethyl)pyrrolo-6-carboxylic acid ethyl ester (650 mg, 82%) as a white solid. LC/MS; (M+H)⁺=264.

B) To a solution of compound A (650 mg, 2.47 mmol) in tetrahydrofuran (10 mL) at −10° C. was added DIBAL in toluene (1.5 M, 3.3 mL) dropwise. The mixture was allowed to warm to RT. After 1 h, it was cooled to 0° C. and a solution of NaHCO₃ (1 mL) was added. The precipitate was then filtered off. The filtrate was concentrated and the residue was purified by flash column chromatography eluting with ethyl acetate in hexanes (1:1) to afford 4-methoxy-[2,1-f][1,2,4]triazin-5-(1-methylethyl)pyrrolo-6-methanol (480 mg, 88%) as a white solid. LC/MS; (M+H)⁺=222.

C) To a solution of compound B (480 mg, 2.17 mmol) in toluene (5 mL) was added MnO₂ (600 mg, 6.9 mmol) and the mixture was refluxed for 5 h. It was then cooled to RT, filtered and the filtrate was concentrated to afford 4-methoxy-[2,1-f][1,2,4]triazin-5-(1-methylethyl)pyrrolo-6-carboxaldehyde (410 mg, 86%) as beige solid. LC/MS; (M+H)⁺=220.

D) To a solution of compound C (219 mg, 1 mmol) in a mixture of dichloromethane/TFA (7/3, 5 mL) at RT was added m-CPBA (300 mg, 57% pure) and the mixture was stirred for 3 h. Saturated NaHCO₃ solution was added followed by sodium thiosulfate (300 mg). The mixture was diluted with ethyl acetate (20 mL), separated and the organics were washed with NaHCO₃ solution, dried and concentrated in vacuo to afford a solid. The solid was dissolved in methanol (10 mL) and stirred with a solution of Na₂CO₃ (2 M, 3 mL) for 2 h. The mixture was neutralized with 1 N HCl and concentrated. The residue was then partitioned between ethyl acetate and water. The ethyl acetate layer was separated, washed with brine, dried and concentrated to afford 6-hydroxy-4-methoxy-[2,1-f][1,2,4]triazin-5-(1-methylethyl)pyrrole (175 mg, 84%) as a white solid. LC/MS; (M+H)⁺=208.

E) To a solution of compound D (38 mg, 0.184 mmol) in dimethyl formamide (0.5 mL) at RT were added K₂CO₃ (50 mg) followed by iodoethane (43 mg, 0.28 mmol). After stirring for 16 h, the mixture was partitioned between ethyl acetate and water. The organic layer was separated, washed with brine, dried, and concentrated. The residue was purified by flash column chromatography eluting with ethyl acetate in hexanes (1:40) to afford 6-ethoxy-4-methoxy-[2,1-f][1,2,4]triazin-5-(1-methylethyl)pyrrole (42 mg, 97%). LC/MS; (M+H)⁺=236.

F) To a solution of compound E (42 mg, 0.18 mmol) in methanol (1 mL) was added 1N HCl (1 mL) and the resulting mixture was refluxed. After 2 h, the mixture was cooled and concentrated. The residue was diluted with water (2 mL) and the precipitate that formed was filtered, washed with water and dried in vacuo to afford 6-ethoxy-5-(1-methylethyl)pyrrolo[2,1-f][1,2,4]triazin-4(3H)-one (31 mg, 78%). LC/MS; (M+H)⁺=222

G) To a solution of compound F (31 mg, 0.14 mmol) in phosphorous oxychloride (0.5 mL) was stirred at 120° C. After 3 h, the mixture was cooled to RT, and concentrated. The residue was dissolved in dichloromethane and washed with saturated NaHCO₃ solution. The organic layer was separated, dried and concentrated in vacuo to afford 4-chloro-6-ethoxy-[2,1-f][1,2,4]triazin-5-(1-methylethyl)pyrrole (32 mg, 95%). LC/MS; (M+H)⁺=236.

H) To a solution of compound G (32 mg, 0.13 mmol) in dimethyl formamide (0.5 mL) were added triethylamine (0.1 mL) and 5-amino-4-fluoro-N-methoxy-2-methylbenzamide (Example 10) (30 mg). The resulting mixture was stirred at RT for 10 h, and the mixture was purified by RP HPLC. The appropriate fractions were collected, concentrated and the residue was partitioned between ethyl acetate and saturated NaHCO₃ solution. The organic layer was separated, dried and concentrated to afford the title compound (10 mg, 20%) as a white solid. LC/MS; (M+H)⁺=402.

Example 28

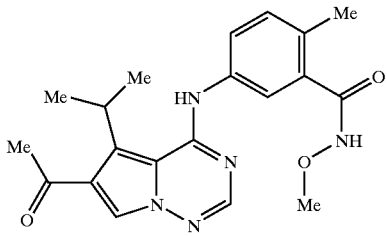

5-[[6-Acetyl-5-(1-methylethyl)pyrrolo[2,1-f][1,2,4]triazin-4-yl]amino]-N-methoxy-2-methylbenzamide A) Example 1 was hydrolyzed to 5-(1-methylethyl)pyrrolo[2,1-f][1,2,4]triazin-4(3H)-one-6-carboxylic acid in a manner similar to that described for the conversion of Example 6 to compound A in Example 18. LC/MS; $(M+H)^+=222.1$.

B) To a solution of compound A (100 mg, 0.45 mmol) in dimethyl formamide (4.5 mL) were added 1-(3-dimethylaminopropyl)-3-ethylcarbodiimide hydrochloride (130 mg, 0.7 mmol), N,O-dimethylhydroxyl amine hydrochloride (49 mg, 0.5 mmol), HOBt (67 mg, 0.5 mmol), and N-methylmorpholine (0.11 mL, 1 mmol. After stirring at ambient temperature overnight, the mixture was poured into ethyl acetate (20 mL) and washed sequentially with saturated solution of $NaHCO_3$, water and 10% aqueous LiCl. The organic layer was separated, dried, and concentrated to afford an oil which was purified by flash silica gel column eluting with 2–5% methanol in $CHCl_3$ to obtain of N,O-dimethyl-5-(1-methylethyl)pyrrolo[2,1-f][1,2,4]triazin-4(3H)-one-6-carboxamide(75 mg, 63%) as a white foam. LC/MS; $(M+H)^+=265.1$ C) To a solution of compound B (39 mg, 0.15 mmol) in tetrahydrofuran (1.5 mL) at −25° C. under argon was added methyl lithium (0.32 mL, 0.45 mmol) dropwise. A white precipitate formed. The mixture was allowed to warm to 0° C., stirred for 20 min. and poured into saturated solution of $NH_4Cl$. The resulting mixture was extracted with ethyl acetate (3×10 mL). The organic layer was washed with brine, dried, concentrated and the residue was purified by flash column chromatography eluting with 2–5% gradient of methanol in chloroform to afford N,O-dimethyl-6-acetyl-5-(1-methylethyl)pyrrolo[2, 1-f][1,2,4]triazin-4(3H)-one-6-carboxamide (25 mg, 78%) as a white solid. LC/MS; $(M+H)^+=220.1$.

D) A solution of compound C (15 mg) in phosphorous oxychloride (1.5 mL) was warmed to 90° C. for 3 h. The mixture was cooled to ambient temperature and concentrated in vacuo. The residue was dissolved in dichloromethane and washed with cold aqueous solution of $NaHCO_3$, dried and concentrated in vacuo. The residue was dissolved in dimethyl formamide (1.5 mL) and 5-amino-2-methyl-N-methoxycarboxamide (35 mg, Example 17) was added. After 3 h at ambient temperature, water (5 ml) was added and the mixture was extracted with ethyl acetate (3×10 mL). The organic layers were combined, washed with 10% LiCl solution, dried and concentrated in vacuo. The resulting oil was purified by flash chromatography eluting with 2–5% gradient of methanol in chloroform to afford the title compound (16 mg, 37% over 2 steps).

Example 29

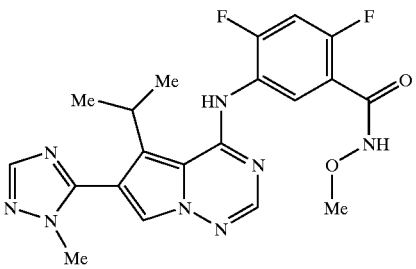

2,4-Difluoro-N-methoxy-5-[[5-(1-methylethyl)-6-(2-methyl-1H-1,2,4-triazol-3-yl)pyrrolo[2,1-f][1,2,4]triazin-4-yl]amino]benzamide A) To a solution of compound A of Example 28 (663 mg, 3 mmol) in dimethyl formamide (10 mL) were added were added successively 1-(3-dimethylaminopropyl)-3-ethylcarbodiimide hydrochloride (670 mg, 3.5 mmol), HOBt (460 mg, 3 mmol), and triethylamine (0.5 mL, 3.5 mmol). After 2 h, aqueous ammonia (1 mL, 6N) was added. After 1 h, the mixture was concentrated and the residue was partitioned between ethyl acetate (30 mL) and aqueous $NaHCO_3$ (15 mL). The organic layer was separated, dried, and concentrated to afford methyl-5-(1-methylethyl)pyrrolo[2,1-f][1,2,4]triazin-4(3H)-one-6-carboxamide (390 mg, 59%) as white solid. LC/MS; $(M+H)^+=221.1$.

B) The above compound A (390 mg, 1.77 mmol) was dissolved in phosphorous oxychloride (3 mL) and warmed to 80° C. for 2 h, and then to 120° C. for 8 h. The mixture was then cooled and concentrated in vacuo, washed with $NaHCO_3$ and extracted with ethyl acetate. The organic layer was dried and concentrated in vacuo to obtain 6-cyano-5-(1-methylethyl)pyrrolo[2,1-f][1,2,4]triazin-4(3H)-one (285 mg, 80%) as a solid. LC/MS; $(M+H)^+=203$.

C) A solution of compound B (101 mg, 0.5 mmol) in ethanol (3 mL) at 0° C. was saturated with HCl gas. After 2 h, the mixture was warmed to RT and stirred for 2 days. The mixture was concentrated in vacuo to afford a white solid which was then redissolved in ethanol (3 mL) and treated with methylhydrazine (0.3 mL). After stirring at RT for 2 h, the mixture was concentrated in vacuo to afford a solid which was then treated with formic acid (2 mL) at 100° C. After 5 h, the mixture was cooled to RT, neutralized with aqueous $NaHCO_3$, and extracted with ethyl acetate (3 times). The combined extracts were concentrated and the residue was purified by flash column chromatography on silica gel eluting with ethyl acetate to afford two isomers. Less polar isomer A, 5-(1-methylethyl)-6-(2-methyl-1H-1,2,4-triazol-3-yl)pyrrolo[2,1-f][1,2,4]triazin-4(3H)-one (60 mg), LC/MS; $(M+H)^+=259$ and Isomer B, 5-(1-methylethyl)-6-(1-methyl-1H-1,2,4-triazol-3-yl)pyrrolo[2,1-f][1,2,4]triazin-4(3H)-one (25 mg), LC/MS; $(M+H)^+=259$.

D) A solution of isomer A (60 mg, 0.23 mmol) in phosphorous oxychloride (3 mL) was heated to reflux. After 3 h, the mixture was cooled to an ambient temperature and concentrated in vacuo. Half of the residue obtained was dissolved in isopropanol (2 mL) and Example 21 (28 mg, 0.14 mmol) was added. The mixture was heated at 80° C. After 1 h, the mixture was concentrated and the residue was purified by preparative RP HPLC eluting with a mixture of methanol in water containing 0.1% TFA. Appropriate fractions were collected, concentrated and treated with 1 N aqueous HCl. The solution was lyophilized to afford the title compound (3.5 mg). The structure was confirmed by NOE NMR experiments. LC/MS; (M+H)+=443.

Example 30

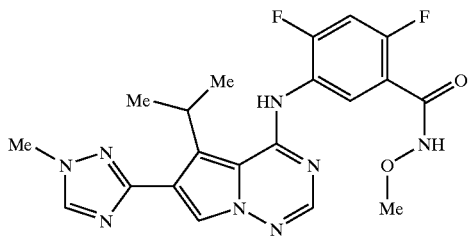

2,4-Difluoro-N-methoxy-5-[[5-(1-methylethyl)-6-(1-methyl-1H-1,2,4-triazol-3-yl)pyrrolo[2,1-f][1,2,4]triazin-4-yl]amino]benzamide Isomer B obtained in the preparation of Example 29 was converted to the title compound in a manner similar to that for the conversion of isomer A to Example 29. LC/MS; (M+H)+=443.1

Example 31

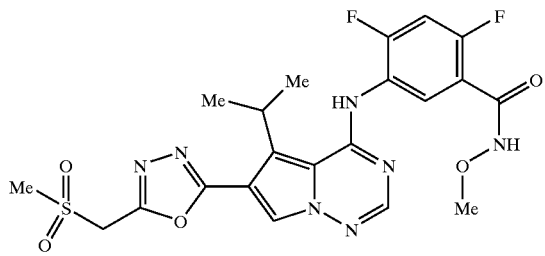

2,4-Difluoro-N-methoxy-5-[[5-(1-methylethyl)-6-[5-[(methylsulfonyl)methyl]-1,3,4-oxadiazol-2-yl]pyrrolo[2,1-f][1,2,4]triazin-4-yl]amino]benzamide A) To a solution of compound A in Example 26 (3 g, 12.8 mmol) in ethanol (49 mL) was added 2-methanesulfonylacetimidic acid ethyl ester HCl salt (2.83 g, 14 mmol) and the mixture was heated at 45° C. After 2 h, the mixture was concentrated and the residue was extracted with ethyl acetate (3 times). The combined extracts were concentrated to give 5-(1-methylethyl)-4-oxo-3,4-dihydro-pyrrolo[2,1-f][1,2,4]triazine-6-carboxylic acid (1-ethoxy-2-methanesulfonyl-ethylidene)-hydrazide (3.7 g, 76%) as a light brown foam.

B) To a solution of compound A (3.7 g, 9.7 mmol) in phosphorous oxychloride (30 mL) was heated at 80° C. After 15 min, the mixture was heated at 120° C. for 1.5 h. The mixture was cooled and concentrated in vacuo. The residue was dissolved in ethyl acetate and washed with saturated NaHCO3, dried (Na2SO4), and concentrated. The residue was dissolved in acetonitrile (50 mL) and Example 21 (1.96 g, 9.7 mmol) was added. After stirring for 16 h, the resulting mixture was concentrated, and the residue was purified by column chromatography on silica gel eluting with 0–5% methanol in chloroform followed by ethyl acetate to afford the title compound (1.99 g, 39%) as a white solid. LC/MS; (M+H)+=522.

Example 32

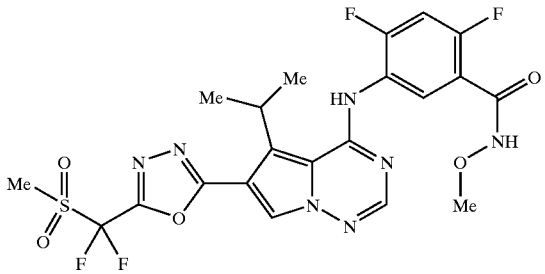

5-[[6-[5-[Difluoro(methylsulfonyl)methyl]-1,3,4-oxadiazol-2-yl]-5-(1-methylethyl)pyrrolo[2,1-f][1,2,4]triazin-4-yl]amino]-2,4-difluoro-N-methoxybenzamide To a solution of Example 31 (0.89 g, 1.71 mmol) in tetrahydrofuran (36 mL) at −78° C., was added a solution of lithium hexamethyldisilazane (1 M) in tetrahydrofuran. The mixture was warmed to −40° C. and a solution of N-fluorobenzene sulfonimide (1.35 g, 4.28 mmol) in tetrahydrofuran (36 mL) was added dropwise over 10 min. After 40 min, the mixture was warmed to 0° C. over 30 min. The mixture was diluted with ethyl acetate and washed with saturated ammonium chloride solution. The organic layer was dried and concentrated to afford a solid. Purification by column chromatography on silica gel eluting with 2% methanol in chloroform afforded the title compound (620 mg, 65%) as a white solid. LC/MS; (M+H)+=558.3

Example 33

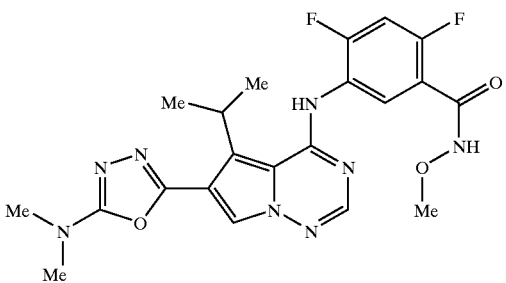

5-[[6-[5-(Dimethylamino)-1,3,4-oxadiazol-2-yl]-5-(1-methylethyl)pyrrolo[2,1-f][1,2,4]triazin-4-yl]amino]-2,4-difluoro-N-methoxybenzamide A) To a solution of compound A in Example 26 (46 mg, 0.2 mmol) in acetonitrile (4 mL) was added phosgene imidinium chloride (38 mg, 0.23 mmol) and the mixture was heated to 80° C. for 2 h. The mixture was cooled to RT, concentrated and the residue was purified by preparative RP HPLC to afford of 5-[[6-[5-(dimethylamino)-1,3,4-oxadiazol-2-yl]-5-(1-methylethyl)pyrrolo[2,1-f][1,2,4]triazin-4(3H)-one (31 mg, 55%). LC/MS; (M+H)+=289.2

B) Compound A (31 mg, 0.11 mmol) was converted to the title compound (11 mg, 48%) by the treatment with Example 21 in a manner similar to that for the conversion of compound C in Example 29 to Example 29. LC/MS; (M+H)+=473.2

Examples 34 to 57

Compounds from Examples 34 to 57 shown in Table II below were synthesized from 4-(2,4-difluoro-5-methoxycarbamoyl-phenylamino)-5-(1-methylethyl)-pyrrolo[2,1-f][1,2,4]triazine-6-carbonyl azide (compound A in Example 23), by an analogous method for the preparation of Example 23, using two equivalents of the appropriate alcohol.

TABLE II

| Example No. | Compound Name | Mass Spec (M + H)+ |
|---|---|---|
| 34 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-(1-methyl-1H-1,2,4-triazol-5-yl)ethyl ester | 530.5 |
| 35 | [4-[[2,4-Difluoro-5-[(methoxyamino)carbonyl]phenyl]amino]-5-(1-methylethyl)pyrrolo[2,1-f][1,2,4]triazin-6-yl]carbamic acid, (1-methyl-4-piperidinyl)methyl | 532.6 |
| 36 | [4-[[2,4-Difluoro-5-[(methoxyamino)carbonyl]phenyl]amino]-5-(1-methylethyl)pyrrolo[2,1-f][1,2,4]triazin-6-yl]carbamic acid, 3-(1H-1,2,3-triazol-1-yl)propyl ester | 530.6 |
| 37 | [4-[[2,4-Difluoro-5-[(methoxyamino)carbonyl]phenyl]amino]-5-(1-methylethyl)pyrrolo[2,1-f][1,2,4]triazin-6-yl]carbamic acid, 2-(1H-1,2,3-triazol-1-yl)ethyl ester | 516.4 |
| 38 | [4-[[2,4-Difluoro-5-[(methoxyamino)carbonyl]phenyl]amino]-5-(1-methylethyl)pyrrolo[2,1-f][1,2,4]triazin-6-yl]carbamic acid, 3-(6-methyl-2-pyridinyl)propyl ester | 554.5 |
| 39 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-(methylsulfonyl)ethyl ester | 527.5 |
| 40 | [4-[[2,4-Difluoro-5-[(methoxyamino)carbonyl]phenyl]amino]-5-(1-methylethyl)pyrrolo[2,1-f][1,2,4]triazin-6-yl]carbamic acid (2-butyl-1H-imidazol-4-yl)methyl ester | 556.5 |
| 41 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-(4-pyridinyl)ethyl ester | 526.4 |
| 42 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-(dimethoxyphosphinyl)ethyl ester | 557.5 |
| 43 | [4-[[2,4-Difluoro-5-[(methoxyamino)carbonyl]phenyl]amino]-5-(1-methylethyl)pyrrolo[2,1-f][1,2,4]triazin-6-yl]carbamic acid (6-methyl-2-pyridinyl)methyl ester | 525.6 |
| 44 | [4-[[2,4-Difluoro-5-[(methoxyamino)carbonyl]phenyl]amino]-5-(1-methylethyl)pyrrolo[2,1-f][1,2,4]triazin-6-yl]carbamic acid [(2S)-1-methyl-2-pyrrolidinyl]methyl ester | 518.5 |
| 45 | [4-[[2,4-Difluoro-5-[(methoxyamino)carbonyl]phenyl]amino]-5-(1-methylethyl)pyrrolo[2,1-f][1,2,4]triazin-6-yl]carbamic acid (1-methyl-2-piperidinyl)methyl ester | 532.6 |
| 46 | [4-[[2,4-Difluoro-5-[(methoxyamino)carbonyl]phenyl]amino]-5-(1-methylethyl)pyrrolo[2,1-f][1,2,4]triazin-6-yl]carbamic acid 1-methyl-4-piperidinyl ester | 518.5 |
| 47 | [4-[[2,4-Difluoro-5-[(methoxyamino)carbonyl]phenyl]amino]-5-(1-methylethyl)pyrrolo[2,1-f][1,2,4]triazin-6-yl]carbamic acid 4-pyridinylmethyl ester | 512.4 |
| 48 | [4-[[2,4-Difluoro-5-[(methoxyamino)carbonyl]phenyl]amino]-5-(1-methylethyl)pyrrolo[2,1-f][1,2,4]triazin-6-yl]carbamic acid 3-pyridinylmethyl ester | 512.5 |
| 49 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-(2-pyridinyl)ethyl ester | 526.5 |
| 50 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-pyridinylmethyl ester | 512.5 |

TABLE II-continued

| Example No. | Compound Name | Mass Spec (M + H)+ |
|---|---|---|
| 51 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-(4-morpholinyl)ethyl ester | 534.5 |
| 52 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-(1-methyl-2-pyrrolidnyl)ethyl ester | 532.6 |
| 53 | [4-[[2,4-Difluoro-5-[(methoxyamino)carbonyl]phenyl]amino]-5-(1-methylethyl)pyrrolo[2,1-f][1,2,4]triazin-6-yl]carbamic acid 1-methyl-3-pyrrolidnyl ester | 504.5 |
| 54 | [4-[[2,4-Difluoro-5-[(methoxyamino)carbonyl]phenyl]amino]-5-(1-methylethyl)pyrrolo[2,1-f][1,2,4]triazin-6-yl]carbamic acid 2-ethoxyethyl ester | 493.5 |
| 55 | [4-[[2,4-Difluoro-5-[(methoxyamino)carbonyl]phenyl]amino]-5-(1-methylethyl)pyrrolo[2,1-f][1,2,4]triazin-6-yl]carbamic acid [5-[(dimethylamino)methyl]-2-furanyl]methyl ester | 558.6 |
| 56 | [4-[[2,4-Difluoro-5-[(methoxyamino)carbonyl]phenyl]amino]-5-(1-methylethyl)pyrrolol[2,1-f][1,2,4]triazin-6-yl]carbamic acid 2-(1-piperidinyl)ethyl ester | 532.6 |
| 57 | [4-[[2,4-Difluoro-5-[(methoxyamino)carbonyl]phenyl]amino)-5-(1-methylethyl)pyrrolo[2,1-f][1,2,4]triazin-6-yl]carbamic acid 3-hydroxybutyl ester | 493.4 |

Example 58

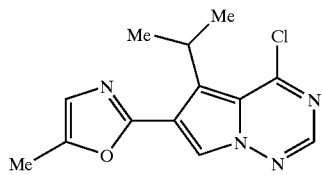

4-Chloro-5-(1-methylethyl)-6-(5-methyl-2-oxazolyl)pyrrolo[2,1-f][1,2,4]triazin

A) To a solution of compound A in Example 28 (200 mg, 0.9 mmol) in dimethyl formamide (7 mL) was added 2-aminoacetone (150 mg, 1.3 mmol) followed by N-methylmorpholine (0.4 mL), and BOP reagent (500 mg, 1.2 mmol). After stirring at the ambient temperature for 19 h, the mixture was dissolved in ethyl acetate and washed with 10% LiCl solution. The organic layer was separated, dried and concentrated in vacuo. The residue was purified by silica gel column chromatography eluting with 5% methanol in chloroform to afford the keto amide, 4-hydroxy-5-(methylethyl)pyrrolo[2,1-f][1,2,4]triazine-6-carboxylic acid (2-oxopropyl)amide (82 mg, 33%). LC/MS; (M+H)+=277.1.

B) A solution of compound A (65 mg, 0.23 mmol) was heated to reflux in phosphorous oxychloride (6 mL) for 8 h. The mixture was cooled, concentrated, and the residue was partitioned between ethyl acetate and cold sodium bicarbonate solution. The organic layer was dried, and concentrated to afford the title compound (65 mg) which was used further without purification.

Example 59

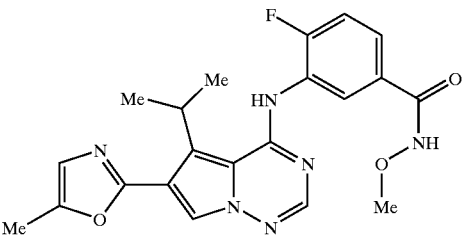

4-Fluoro-N-methoxy-3-[[5-(1-methylethyl)-6-(5-methyl-2-oxazolyl)pyrrolo[2,1-f][1,2,4]triazin-4-yl]amino]benzamide A) To a solution of Example 58 (30 mg, 0.11 mmol) in dimethyl formamide (0.7 mL) at RT was added 3-amino-4-fluoro-N-methoxy-benzamide (30 mg, 0.16 mmol). After stirring at ambient temperature for 19 h, the mixture was dissolved in ethyl acetate and washed with 10% LiCl solution. The organic layer was separated, dried and concentrated in vacuo. The residue was purified by silica gel column chromatography eluting with 5% methanol in chloroform to afford the title compound (22 mg, 48%) as an off-white solid. LC/MS; (M+H)+=425.1.

Examples 60 to 64

Examples 60 to 64 shown in Table III were synthesized from Example 58 using an appropriate aniline by a procedure analogous to that for the preparation of Example 59.

TABLE III

| Example No. | Compound | LC/MS; (M + H)+ |
|---|---|---|
| 60 | 2,4-Difluoro-N-methoxy-5-[[5-(1-methylethyl)-6-(5-methyl-2-oxazolyl)pyrrolo[2,1-f][1,2,4]triazin-4-yl]amino]benzamide | 444.3 |
| 61 | 2-Fluoro-N-methoxy-5-[[5-(1-methylethyl)-6-(5-methyl-2-oxazolyl)pyrrolo[2,1-f][1,2,4]triazin-4-yl]amino]benzamide | 425.1 |
| 62 | N-Methoxy-2-methyl-5-[[5-(1-methylethyl)-6-(5-methyl-2-oxazolyl)pyrrolo[2,1-f][1,2,4]triazin-4-yl]amino]benzamide | 421.1 |
| 63 | 4-Fluoro-N-methoxy-2-methyl-5-[[5-(1-methylethyl)-6-(5-methyl-2-oxazolyl)pyrrolo[2,1-f][1,2,4]triazin-4-yl]amino]benzamide | 439 |
| 64 | 2-Chloro-N-methoxy-5-[[5-(1-methylethyl)-6-(5-methyl-2-oxazolyl)pyrrolo[2,1-f][1,2,4]triazin-4-yl]amino]benzamide | 441.1 |

Example 65

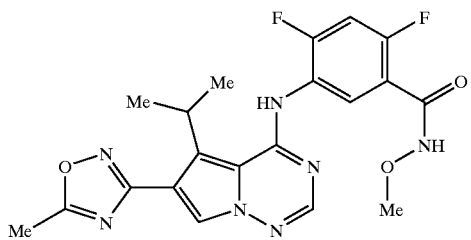

2,4-Difluoro-N-methoxy-5-[[5-(1-methylethyl)-6-(5-methyl-1,2,4-oxadiazol-3-yl)pyrrolo[2,1-f][1,2,4]triazin-4-yl]amino]benzamide A) To a solution of 6-cyano-5-(1-methylethyl)pyrrolo[2,1-f][1,2,4]triazin-4(3H)-one (compound B in Example 29) (70 mg, 0.35 mmol) in ethanol (4 mL) were added potassium carbonate (23 mg, 1.7 mmol) and hydroxylamine hydrochloride (73 mg, 1 mmol) and the resulting mixture was refluxed. After 15 h, more hydroxylamine hydrochloride (2 equivalent) was added. After a total of 26 h, the mixture was cooled, water was added and the mixture was extracted with ethyl acetate. The organic layer was washed with brine, dried and concentrated. The residue was purified by silica gel flash column chromatography eluting with 5% methanol in chloroform to afford a solid which was dissolved in pyridine and treated with acetyl chloride (4 equivalent). The mixture was stirred at 120° C. for 7 h, cooled to RT, dissolved in ethyl acetate and washed with water, 1 N NaOH solution and 1N HCl. The organic layer was dried, concentrated and the residue was purified by silica gel column eluting with 5% methanol in chloroform to afford 5-(1-methylethyl)-6-(5-methyl-[1,2,4]oxadiazol-3-yl)pyrrolo[2,1-f][1,2,4]triazin-4-ol (10 mg, 11% over two steps) as a white solid. LC/MS; (M+H)+=260.2.

B) Compound A (8 mg, 0.03 mmol) was converted to the title compound (1 mg, 10%) as a white solid by treatment with Example 21 in a manner similar to that for the conversion of compound C in Example 29 to Example 29. LC/MS; (M+H)+=444.2.

What is claimed is:

1. A compound selected from the group consisting of

[4-[[2,4-Difluoro-5-[(methoxyamino)carbonyl]phenyl]amino]-5-(1-methylethyl)pyrrolo[2,1-f][1,2,4]triazin-6-yl]carbamic acid 3-(methylsulfonyl)propyl ester,

[4-[[2,4-Difluoro-5-[(methoxyamino)carbonyl]phenyl]amino]-5-(1-methylethyl)pyrrolo[2,1-f][1,2,4]triazin-6-yl]carbamic acid 3-(1-piperidinyl)propyl ester, 5-[[6-[5-(Difluoromethyl)-1,3,4-oxadiazol-2-yl]-5-(1-methylethyl)pyrrolo [2,1-f][1,2,4]triazin-4-yl]amino]-2,4-difluoro-N-methoxybenzamide, 2,4-Difluoro-N-methoxy-5-[[5-(1-methylethyl)-6-(2-methyl-1H-1,2,4-triazol-3-yl)pyrrolo[2,1-f][1,2,4]triazin-4-yl]amino]benzamide, 2,4-Difluoro-N-methoxy-5-[[5-(1-methylethyl)-6-[5-[(methylsulfonyl)methyl]-1,3,4-oxadiazol-2-yl]pyrrolo[2,1-f][1,2,4]triazin-4-yl]amino]benzamide, 5-[[6-[5-[Difluoro(methylsulfonyl)methyl]-1,3,4-oxadiazol-2-yl]-5-(1-methylethyl)pyrrolo[2,1-f][1,2,4]triazin-4-yl]amino]-2,4-difluoro-N-methoxybenzamide, 5-[[6-[5-(Dimethylamino)-1,3,4-oxadiazol-2-yl]-5-(1-methylethyl)pyrrolo[2,1-f][1,2,4]triazin-4-yl]amino]-2,4-difluoro-N-methoxybenzamide, 4-Fluoro-N-methoxy-3-[[5-(1-methylethyl)-6-(5-methyl-2-oxazolyl)pyrrolo[2,1-f][1,2,4]triazin-4-yl]amino]benzamide, 2,4-Difluoro-N-methoxy-5-[[5-(1-methylethyl)-6-(5-methyl-2-oxazolyl)pyrrolo[2,1-f][1,2,4]triazin-4-yl]amino]benzamide, and 2,4-Difluoro-N-methoxy-5-[[5-(1-methylethyl)-6-(5-methyl-1,2,4-oxadiazol-3-yl)pyrrolo[2,1-f][1,2,4]triazin-4-yl]amino]benzamide, or a pharmaceutically acceptable salt thereof.

2. A pharmaceutical composition comprising one or more of the compounds of claim 1 and a pharmaceutically acceptable carrier.

* * * * *